(12) United States Patent
Kossida

(10) Patent No.: US 6,908,743 B2
(45) Date of Patent: Jun. 21, 2005

(54) ISOLATED HUMAN INOSITOL POLYPHOSPHATE 5-PHOSPHATASE

(75) Inventor: Sophia Kossida, Basel (CH)

(73) Assignee: Bayer Aktiengesellschaft, Leverkusen (DE)

( * ) Notice: Subject to any disclaimer, the term of this patent is extended or adjusted under 35 U.S.C. 154(b) by 76 days.

(21) Appl. No.: 10/415,147

(22) PCT Filed: Oct. 29, 2001

(86) PCT No.: PCT/EP01/12496
§ 371 (c)(1),
(2), (4) Date: Apr. 25, 2003

(87) PCT Pub. No.: WO02/36755
PCT Pub. Date: May 10, 2002

(65) Prior Publication Data
US 2004/0043399 A1 Mar. 4, 2004

Related U.S. Application Data

(60) Provisional application No. 60/314,660, filed on Aug. 27, 2001, provisional application No. 60/257,302, filed on Dec. 26, 2000, and provisional application No. 60/243,745, filed on Oct. 30, 2000.

(51) Int. Cl.⁷ .......................... C12N 9/16; C12N 15/00; C12Q 1/42; C12P 21/36; A61K 38/46
(52) U.S. Cl. ...................... 435/21; 435/196; 435/320.1; 435/69.1; 536/23.2; 530/350; 424/94.6
(58) Field of Search ...................... 435/196, 21, 320.1, 435/69.1; 536/23.2; 530/350; 424/94.6

(56) References Cited
U.S. PATENT DOCUMENTS
2004/0030110 A1 * 2/2004 Guo et al. ................. 536/23.1

OTHER PUBLICATIONS

Sulston et al., EMBL accession No. AAD15618, Mar. 1999.*
Seffernick et al., J. Bacteriol. 183(8):2405–2410, 2001.*
Broun et al., Science 282:1315–1317, 1998.*
Witkowski et al., Biochemistry 38:11643–11650, 1999.*
Database Swall "Online" Nov. 1, 1996 "Phosphatidylinositol (4, 5) biphosphate 5–phosphatase homolog (Fragment)" Database accession No. Q15735.
Database EMBL "Online" Jul. 8, 1996 "Human phosphatidylinositol (4,5) biphosphate 5–phosphatase homolog mRNA; partial cds" Database accession No. U45975.
Mochizuki Yasuhiro et al: "Novel inositol polyphosphate 5–phosphatase localizes at membrane ruffles." Journal of Biological Chemistry, vol. 274, No. 51, Dec. 17, 1999, pp. 36790–36795.
Mochizuki et al., "Novel inositol polyphosphate 5–phosphatase localizes at membrane ruffles," J Biol chem. 275, pp. 20956 (2000) Erratum.
Database Swall "ONLINE" Oct. 1, 2000 "Proline–rich inositol polyphosphate 5–phosphatase" Database accession No. Q9JMC1.
Database EMBL "Online" Feb. 6, 2000 "Rattus norvegicus PIPP mRNA for proline–rich inositol polyphosphate 5–phosphatase, complete cds" Database accession No. AB032551.
Database Swall "Online" May 1, 2000 "WUGSC:H_ DJ412A9.2 protein" Database accession No. 09UDT9.
Database EMBL "Online" Jun. 15, 1998 "*Homo sapiens* PAC clone RP3–412A9 from 22, complete sequence" Database accession No. AC005005.
Erneux C et al: "The diversity and possible functions of the inositol polyphosphate 5–phosphatases" Biochimica et Biophysica Acta, vol. 1436, No. 1–2, pp. 185–199, Dec. 8, 1998.
Kudo et al., "Localization of mRNA and SHIP2, SH2 domain–containing inositol polyphosphate 5–phosphatase in the brain of developing and mature rats," Brain Res Mol Brain Res 75, pp 172–177 (2000).
Safrany et al., "Design of potent and selective inhibitors of myo–inositol 1,4,5–trisphosphate 5–phosphatase," Biochemistry 33, pp. 10763–10769 (1994).
Speed et al., "Tissue distribution and intracellular localization of the 75–kDa inositol polyphosphate 5–phosphatase," Eur J Biochem 234, pp. 216–224, 1995.

* cited by examiner

*Primary Examiner*—Rebecca E. Prouty
*Assistant Examiner*—Delia M. Ramirez
(74) *Attorney, Agent, or Firm*—Banner & Witcoff, Ltd.

(57) ABSTRACT

Reagents which regulate human inositol polyphosphate 5-phosphatase and reagents which bind to human inositol polyphosphate 5-phosphatase gene products can play a role in preventing, ameliorating, or correcting dysfunctions or diseases including, but not limited to, COPD, asthma, diabetes, and cancer.

5 Claims, 14 Drawing Sheets

Fig. 1

```
atgccaaaagagaggcaaacaccaggttcttataatgtcgtcgtctggttcct
aactgtggtgatgaagcatagttacactggtgaagttgaagtcattgatgatc
acagagctaggaaaactgctgtgaacctcacaggcagggaagccctcccagat
aacccctttctttcacattcccacaatatcctgtatcaccctctacacctttgc
agatggtagccatagcatgacctccctcatggcgggcctgggtcaggtgacc
agggagagaaaggaaggaggacagaccctcggtaccgttgccatcctcaggct
gggaagtgggagcctgtgcctttaaattctcagcaggttgaaatggctgatga
catcactggttcccgggagcggatcactgtggtcacatggaacgtgggcactg
ccatgccccagacgatgtcacatcctcctccacctgggcggtggtgacgac
agcgacggcgcagacatgatcgccatagggttgcaggaagtgaactccatgct
caacaagcgactcaaggacgccctcttcacggaccagtggagtgagctgttca
tggatgcgctagggcccttcaacttcgtgctggtaacgcacccctcaccccct
ggacagccagagaccctgctgaattcctggctccagctgtaccctggctcact
gtggggcccgctgggcctctgtggctgggtgagttcggtgaggatgcagggtg
tcatcctgctgctgttcgccaagtactaccacctgcccttcctgcgagacgtg
cagaccgactgcacgcgcactggcctggcggctactggggtaacaagggtgg
cgtgagcgtgcgcctggcggccttcgggcacatgctctgcttcctgaactgcc
acttgcctgcgcatatggacaaggcggagcagcgcaaagacaacttccagacc
atcctcagcctccagcagttccaagggccgggcgcacagggcatcctggatca
tgagtatgggctggcctcgtgttctggttcggggacctgaacttccgcattg
agagctatgacctgcactttgtcaagtttgccatcgacagtgaccagctccat
cagctctgggagaaggaccagctcaacatggccaagaacacctggcccattct
gaagggctttcaggaggggcccctcaacttcgctcccaccttcaagtttgatg
tgggtaccaacaaatacgataccagtgccaagaaacggaagccagcttggaca
gaccgtatcctatggaaggtcaaggctccaggtgggggtcccagcccctcagg
acggaagagccaccgactccaggtgacgcagcacagctaccgcagccacatgg
aatacacagtcagcgaccacaagcctgtggctgcccagttcctcctgcagttt
gccttcagggacgacatgccactggtgcggctggaggtggcagatgagtgggt
gcggcccgagcaggcggtggtgaggtaccgcatggaaacagtgttcgcccgca
gctcctgggactggatcggcttataccgggtgggtttccgccattgcaaggac
tatgtggcttatgtctgggccaaacatgaagatgtggatgggaatacctacca
ggtaacattcagtgaggaatcactgcccaagggccatggagacttcatcctgg
gctactatagtcacaaccacagcatcctcatcggcatcactgaaccctccag
atctcgctgccttcctcggagttggccagcagcagcacagacagctcaggcac
cagctcagagggagaggatgacagcacactggagctccttgcacccaagtccc
gcagcccagtcctggcaagtccaagcgacaccgcagccgcagccgggactg
gccaggttccctgggcttgccctacggccctcatcccgtgaacgccgtggtgc
cagccgtagcccctcaccccagagccgccgcctgtcccgagtggctcctgaca
ggagcagtaatggcagcagccggggcagtagtgaagagggccctctggttg
cctggcccctgggccttccaccagctgtgcctcgaagcctgggcctgttgcc
cgccttgcgcctagagactgtagaccctggtggtggtggctcctggggacctg
atcgggaggccctggcgcccaacagcctgtctcctagtccccagggccatcgg
gggctggaggaaggggggcctggggccctga
```

Fig. 2

MPKERQTPGSYNVVVWFLTVVMKHSYTGEVEVIDDHRARKTAVNLTGREALPD
NPFFHIPTISCITLYTFADGSHSMTSLMAGLGQGDQGEKGRRTDPRYRCHPQA
GKWEPVPLNSQQVEMADDITGSRERITVVTWNVGTAMPPDDVTSLLHLGGGDD
SDGADMIAIGLQEVNSMLNKRLKDALFTDQWSELFMDALGPFNFVLVTHPSPP
GQPETLLNSWLQLYPGSLWGPLGLCWVSSVRMQGVILLLFAKYYHLPFLRDV
QTDCTRTGLGGYWGNKGGVSVRLAAFGHMLCFLNCHLPAHMDKAEQRKDNFQT
ILSLQQFQGPGAQGILDHEYGLGLVFWFGDLNFRIESYDLHFVKFAIDSDQLH
QLWEKDQLNMAKNTWPILKGFQEGPLNFAPTFKFDVGTNKYDTSAKKRKPAWT
DRILWKVKAPGGGPSPSGRKSHRLQVTQHSYRSHMEYTVSDHKPVAAQFLLQF
AFRDDMPLVRLEVADEWVRPEQAVVRYRMETVFARSSWDWIGLYRVGFRHCKD
YVAYVWAKHEDVDGNTYQVTFSEESLPKGHGDFILGYYSHNHSILIGITEPFQ
ISLPSSELASSSTDSSGTSSEGEDDSTLELLAPKSRSPSPGKSKRHRSRSPGL
ARFPGLALRPSSRERRGASRSPSPQSRRLSRVAPDRSSNGSSRGSSEEGPSGL
PGPWAFPPAVPRSLGLLPALRLETVDPGGGGSWGPDREALAPNSLSPSPQGHR
GLEEGGLGP

Fig. 3

MEGQSRSGSAKSGTRTGLGPLPGTHGALQTGTPSKKVNSSFQLPAFTKNTGPT
PSEPRLALAPVGPRAAVSPPSERPRLALSSPRPILAPLSTAGEQKRPPPHRSS
KPAPTSVGQLVVSAAAGPKPPPVASVSILAPKSLGQLVISASAMPRPTPAPLG
PILSPTSRDQKQLSPTSVGPKPALATSGLSLALASQEQPPQSPSSPSPVPSPV
LSPSQESHLAPATVTSTPASERQLPARQKDTAVRRPIPPADGCLHTPVQAAGL
ATSPPRAQTSSDPRLSPSFRARPEAPRHSPEDPVLPPPPQTLPLDVSSGLPES
GTRSPGLLSPTFRPGIPSNQTVPPPLPKPPRSPSRSPSRSPNRSPCVPPAPEV
ALPRPVTQGAGPGKCPSPNLQTQESPVATATSPTSSWSAQPTCKSDPGFRITV
VTWNVGTAMPPDDVTSLLHLGGGHDSDGADMIAIGLQEVNSMINKRLKDALFT
DQWSELFMDALGPFNFVLVSTVRMQGVILLLFAKYYHLPFLRDVQTDCTRTGL
GGYWGNKGGVSVRLAAFGHMLCFLNCHLPAHMDKAEQRKDNFQTILSLQQFQG
PGAHGILDHDLVFWFGDLNFRIESYDLHFVKFAIDSNQLHQLWEKDQLNMAKN
TWPILKGFQEGPLNFAPTFKFDVGTNKYDTSAKKRKPAWTDRILWKVKAPSGG
PSPSGRESHRLQVTQHSYRSHMEYTVSDHKPVAARFLLQFAFRDDVPLVRLEV
ADEWARPEQAVVRYRVETVFARSSWDWIGLYRVGFRHCKDYVAYVWAKHEEVD
GNIYQVTFSEESLPKGHGDFILGYYSHHHSILIGVTEPFQISLPTSESASSST
DSSGTSSEGEDDSTLELLAPKSRSPSPGKSKRHRSRSPGLARFPSLALRPSSR
ERRGGSRSPSPQSRQLPRVAPDRGHSSGSRGSSEEGPSGPPGPWAFPPAVPRS
LGLLPALRLETVDPGGGGSWGPDQEAPDPNSLSPSPQGRLGLEDGGLGP

Fig. 4

GCGATGAGTGCGTGCGGCCGAGCCAGGCGGTGGTGAGGTACCGCATGGAAACA
GTGTTCGCCCGCAGCTCCTGGGACTGGATCGGCTTATACCGGGTGGGTTTCCG
CCATTGCAAGGACTATGTGGCTTATGTCTGGGCCAAACATGAAGATGTGGATG
GGAATACCTACCAGGTAACATTCAGTGAGGAATCACTGCCCAAGGGCCATGGA
GACTTCATCCTGGGCTACTATAGTCACAACCACAGCATCCTCATCGGCATCAC
TGAACCCTTCCAGATCTCGCTGCCTTCCTCGGAGTTGGCCAGCAGCAGCACAG
ACAGCTCAGGCACCAGCTCAGAGGGAGAGGATGACAGCACACTGGAGCTCCTT
GCACCCAAGTCCCGCAGCCCCAGTCCTGGCAAGCCCAAGCGACACCGCAGCCG
CAGGCCGGGACTGGCCAGGTTCACTGGGCTTGCCCTACGG

Fig. 5

AAGCGGATGAGGGGTGCGGCCGAGTAGGCGGTGGTGAGGTACCGCATGGAAAC
AGTGTTCGCCCGCAGCTCCTGGGACTGGATCGGCTTATACCGGGTGGGTTTCC
GCCATTGCAAGGACTATGTGGCTTATGTCTGGGCCAAACATGAAGATGTGGAT
GGGAATACCTACCAGGTAACATTCAGTGAGGAATCACTGCCCAAGGGCCATGG
AGACTTCATCCTGGGCTACTATAGTCACAACCACAGCATCCTCATCGGCATCA
CTGAACCCTTCCAGATCTCGCTGCCCTCCTCGGAGTTGGCCAGCAGCAGCACA
GACAGCTCAGGCACCAGCTCAGAGGGAGAGGATGACAGCACACTGGAGCTCCT
TGCACCCAAGTCCCGCAGCCCCAGTCCTGGCAAGTCCAAGCGACACCGCAGCC
GCAGCCCGGGACTGGCCAGGTTCCCTGGGCTTGCCCTACGG

Fig. 6

TTGGATAAAGCGGATAGGGGTGCGGCCGAGTAGGCGGTGGTGAGGTACGCATG
GAAACAGTGTTCGCCCGCAGCTCCTGGGACTGGATCGGCTTATACCGGGTGNG
TTTCCGCCATTGCAAGGACTATGTGGCTTATGTCTGGGCCAAACATGAAGATG
TGGATGGGAATACCTACCAGGTAACATTCAGTGAGGAATCACTGCCCAAGGGC
CATGGAGACTTCATCCTGGGCTACTATAGTCACAACCACAGCATCCTCATCGG
CATCACTGAACCCTTCCAGATCTCGCTGCCCTCCTCGGAGTTGGCCAGCAGCA
GCACAGACAGCTCAGGCACCAGCTCAGAGGGAGAGGATGACAGCACACTGGAG
CTCCTTGCACCCAAGTCCCGCAGCCCCAGTCCTGGCAAGTCCAAGCGACACCG
CAGCCGCAGCCCGGGACTGGCCAGGTTCCCTGGGCTTGCCCTACGG

Fig. 7

CTGCACTTTGTCAAGTTTGCCATCGACAGTGACCAGCTCCATCAGCTCTGGGA
GAAGGACCAGCTCAACATGGCCAAGAACACCTGGCCCATTCTGAAGGGCTTTC
AGGAGGGGCCCCTCAACTTCGCTCCCACCTTCAAGTTTGATGTGGGTACCAAC
AAATACGATACCAGTGCCAAGAAACGGAAGCCAGCTTGGACAGACCGTATCCT
ATGGAAGGTCAAGGCTCCAGGTNGGGGTCCCAGCCCCTCAGGACGGAAGAGCC
ACCGACTCCAGGTGACGCAGCACAGCTACCGCAGCCACATGGAATACACAGTC
AGCGACCACAAGCCTGTGGTGNCCCAGTTCCTCCTGGCAGTTTGCCTTTCAGG
GACGACATGCCACTGGTGNCGGCTGGAGGTTGGCAGATTGAGTGGGTTGCGGC
CCGAGCAGGCGGTGGTGAGGTTACCGCTTGGGAAACATTTTTCGNCCGCAGTT
CCTGGGGA

Fig. 8

AANTTTGCCATCGACAGTGACCAGCTCCATCAGCTCTNGGAGAAGGACCAGCT
CAACATGGCCAAGAACACCTGGCCCATTCTGAAGGGCTTTCAGGAGGGGCCCC
TCAACTTCGCTCCCACCTTCAAGTTTGATGTGGGTACCAACAAATACGATACC
AGTGCCAAGAAACGGAAGCCAGCTTGGACAGACCGTATCCTATGGAAGGTCAA
GGCTCCAGGTGGGGGTCCCAGCCCCTCAGGACGGAAGAGCCACCGACTCCAGG
TGACGCAGCACAGCTACCGCAGCCACATGGAATACACAGTCAGCGACCACAAG
CCTGTGGTTGACCCAGTTCCTCCTGCAGTTTTGCCTTTCAGGGGACGGACATT
GCCACTGGTAGCGGCTGGGAGGTGGGCAGATGAGTNGGGTGCGGGCCCGAGCA
GGCGGTNGGTGAGGTTACCGCTTGGGAAACATTTTTTCGGCCGT

Fig. 9

GAGGCTGGAGAATTTAATTCCTAATGGATGACCTCCAGGAGGGGGACATTTGC
CAGAGCTCTCCCATCATCCCAGATGGGGGCCTGGGTGGGGCTTTGCTGATTGT
CACAGTTGAGGTGCCAGGACTGAGTTTTGGGGGACCCCAGTTGTCCACCCCTG
GCCAGGACAGAGAGGCAGGTGCAGATACAGCTGGAGGAGCAGCAGGAGAGAGG
CAGGTGGGCTTGCAAAAGATTGAGGCAGAATGGTGGTCACCTTTGGCCCATCT
GCCTACCCCACCCTCAGGGCCCCAGGCCCCCTTCCTCCAGCCCCGATGGCCC
TGGGACTAGGAGACAGGCTGTTGGGCGCCAGGGCCTCCCGATCAGGTCCCCA
GGAGCCACCACCACCAGGGTCTACAGTCTCTAGGCGCAAGGCGGGCAACAGGC
CCAGGCTTCGAGGCACAGCTGGTGGGAAGGCCCAGGGGCCAGGCAACCCAGAG
GGCCCCTCTTCACTACTGCCCCGGCTGCTGCCATTACTGCTCCTGTCAGGANG
CCACTCGGACAGGCGGCGGCTCTTGGGTGAGGGGCTACGGCTGGCACCACGGC
GTTCACGGNATGAGGGCCGTAGGGCAAGCCCCAGGAACCTGCCAGTCCCGGGC
TGCGGCTGCGTGTCGCTTGGACTTTGCCAGACTGGNGCTGCNGNACCTTGGTG
CAAGGAGCTCCAGTGTGCTGTC

Fig. 10

CGACAGTGACCAGCTCCATCAGCTCTGGGAGAAGGACCAGCTCAACATGGCCA
AGAACACCTGGCCCATTCTGAAGGGCTTTCAGGAGGGGCCCCTCAACTTCGCT
CCCACCTTCAAGTTTGATGTGGGTACCAACAAATACGATACCAGTGCCAAGAA
ACGGAAGCCAGCTTGGACAGACCGTATCCTATGGAAGGTCAAGGCTCCAGGTG
GGGGTCCCAGCCCCTACAGGACGGAAGAGCCACCGACTCCAGGTGACGCAGCA
CAGCTTACCGNAGNCCACATGGAATTACACAGTTCAGGCGACCACAAGGCCT
GTGGCTGACCCCAGTTTCCTCCTTGCAGTTTTGNCTTTCAGGGGACGGACAT
GNCCCATTGGGTTACGGNTTGGGGAGGTTCGNCCAGGTTGCAG

Fig. 11

```
atggagggccagagcagcaggggcagcaggaggccagggacccgggctggcct
gggttccctgcccatgcccagggtgttgcccaaactggggcaccctccaagg
tggactcaagttttcagctcccagcaaagaagaacgcagccctaggaccctcg
gaaccaaggttggctctggcacctgtagggccacgggcagctatgtcagcttc
ctcggaaggaccgaggctggctctggcatctccccgaccaatcctggctccac
tgtgtacccctgaagggcagaaaacagctactgccaccgcagctccagcctg
gccccaacatctgtgggccagctggtgatgtctgcctcagctggaccaaagcc
tcccccagcgaccacaggctcagttctggctccgacgtcctggggctggtga
tgcctgcctcagcagggccaagatctcccccagtcaccctggggcccaatctg
gccccaacctccagagaccagaagcaggagccacctgcctccgtgggacccaa
gccaacactggcagcctctggcctgagcctggccctggcttctgaggagcagc
ccccagaactcccctccacccttccccggtgcccagtccagttctgtctcca
actcaggaacaggccctggctccagcatccacggcatcaggcgcagcctctgt
gggacagacatcagctagaaagagggatgccccagcccctagacctctccctg
cttctgaggggcatctccagcctccagctcagacatctggtcctacaggctcc
ccaccctgcatccaaacctcccagaccctcggctctcccctccttccgagc
ccggcctgaggccctccacagcagccctgaggatcctgttttgccacggccac
cccagaccttgccttggatgtgggccagggtccttcagagcctggcactcac
tcccctggacttctgtccccaccttccggcctggggcccctcaggccagac
tgtgccccacctctgcccaagccaccccgatcacccagccgttccccaagcc
actccccgaatcgctctcctgtgttccccagcccctgacatggccctccca
aggcttggcacacagagtacagggcctggcaggtgcctgagccccaaccttca
ggcccaagaagccccagccccagtcaccacctcctcttctacatccaccctgt
catcctcccttggtcagctcagcctacctggaagagcgaccccggcttccgg
atcactgtggtcacatggaacgtgggcactgccatgccccagacgatgtcac
atccctcctccacctgggcggtggtgacgacagcgacggcgcagacatgatcg
ccatagggttgcaggaagtgaactccatgctcaacaagcgactcaaggacgcc
ctcttcacggaccagtggagtgagctgttcatggatgcgctagggcccttcaa
cttcgtgctggtgagttcggtgaggatgcagggtgtcatcctgctgctgttcg
ccaagtactaccacctgccttcctgcgagacgtgcagaccgactgcacgcgc
actggcctgggcggctactggggtaacaagggtggcgtgagcgtgcgcctggc
ggccttcgggcacatgctctgcttcctgaactgccacttgcctgcgcatatgg
acaaggcggagcagcgcaaagacaacttccagaccatcctcagcctccagcag
ttccaagggccgggcgcacagggcatcctggatcatgacctcgtgttctggtt
cggggacctgaacttccgcattgagagctatgacctgcactttgtcaagtttg
ccatcgacagtgaccagctccatcagctctgggagaaggaccagctcaacatg
gccaagaacacctggcccattctgaagggctttcaggaggggcccctcaactt
cgctcccaccttcaa
```

Fig. 11 (continued)

```
gtttgatgtgggtaccaacaaatacgataccagtgccaagaaacggaagccag
cttggacagaccgtatcctatggaaggtcaaggctccaggtgggggtcccagc
ccctcaggacggaagagccaccgactccaggtgacgcagcacagctaccgcag
ccacatggaatacacagtcagcgaccacaagcctgtggctgcccagttcctcc
tgcagtttgccttcagggacgacatgccactggtgcggctggaggtggcagat
gagtgggtgcggcccgagcaggcggtggtgaggtaccgcatggaaacagtgtt
cgcccgcagctcctgggactggatcggcttataccgggtgggtttcgccatt
gcaaggactatgtggcttatgtctgggccaaacatgaagatgtggatgggaat
acctaccaggtaacattcagtgaggaatcactgcccaagggccatggagactt
catcctgggctactatagtcacaaccacagcatcctcatcggcatcactgaac
ccttccagatctcgctgccttcctcggagttggccagcagcagcacagacagc
tcaggcaccagctcagagggagaggatgacagcacactggagctccttgcacc
caagtcccgcagcccagtcctggcaagtccaagcgacaccgcagccgcagcc
cgggactggccaggttcctgggcttgcctacggccctcatccgtgaacgc
cgtggtgccagccgtagcccctcacccagagccgccgcctgtcccgagtggc
tcctgacaggagcagtaatggcagcagccggggcagtagtgaagaggggccct
ctgggttgcctggccctgggccttccaccagctgtgcctcgaagcctgggc
ctgttgccgccttgcgcctagagactgtagacctggtggtggtggctcctg
gggacctgatcgggaggccctggcgcccaacagcctgtctcctagtccccagg
gccatcgggggctggaggaagggggcctggggccc
```

Fig. 12

```
MEGQSSRGSRRPGTRAGLGSLPMPQGVAQTGAPSKVDSSFQLPAKKNAALGPS
EPRLALAPVGPRAAMSASSEGPRLALASPRPILAPLCTPEGQKTATAHRSSSL
APTSVGQLVMSASAGPKPPPATTGSVLAPTSLGLVMPASAGPRSPPVTLGPNL
APTSRDQKQEPPASVGPKPTLAASGLSLALASEEQPPELPSTPSPVPSPVLSP
TQEQALAPASTASGAASVGQTSARKRDAPAPRPLPASEGHLQPPAQTSGPTGS
PPCIQTSPDPRLSPSFRARPEALHSSPEDPVLPRPPQTLPLDVGQGPSEPGTH
SPGLLSPTFRPGAPSGQTVPPPLPKPPRSPSRSPSHSPNRSPCVPPAPDMALP
RLGTQSTGPGRCLSPNLQAQEAPAPVTTSSSTSTLSSSPWSAQPTWKSDPGFR
ITVVTWNVGTAMPPDDVTSLLHLGGGDDSDGADMIAIGLQEVNSMLNKRLKDA
LFTDQWSELFMDALGPFNFVLVSSVRMQGVILLLFAKYYHLPFLRDVQTDCTR
TGLGGYWGNKGGVSVRLAAFGHMLCFLNCHLPAHMDKAEQRKDNFQTILSLQQ
FQGPGAQGILDHDLVFWFGDLNFRIESYDLHFVKFAIDSDQLHQLWEKDQLNM
AKNTWPILKGFQEGPLNFAPTFKFDVGTNKYDTSAKKRKPAWTDRILWKVKAP
GGGPSPSGRKSHRLQVTQHSYRSHMEYTVSDHKPVAAQFLLQFARDDMPLVR
LEVADEWVRPEQAVVRYRMETVFARSSWDWIGLYRVGFRHCKDYVAYVWAKHE
DVDGNTYQVTFSEESLPKGHGDFILGYYSHNHSILIGITEPFQISLPSSELAS
SSTDSSGTSSEGEDDSTLELLAPKSRSPSPGKSKRHSRSPGLARFPGLALRP
SSRERRGASRSPSPQSRRLSRVAPDRSSNGSSRGSSEEGPSGLPGWAFPPAV
PRSLGLLPALRLETVDPGGGSWGPDREALAPNSLSPSPQGHRGLEEGGLGP
```

Fig. 13

BLASTP - alignment of 249_PR against trembl|AB032551|AB032551_1
gene: "PIPP"; product: "proline-rich inositol polyphosphate 5-phosphatase";
Rattus norvegicus PIPP mRNA for proline-rich inositol polyphosphate 5-
phosphatase, complete cds. //:gp|AB032551|6906704 gene: "PIPP"; product:
"proline-rich inositol polyphosphate 5-phosphatase"; Rattus norvegicus PIPP
mRNA for proline-rich inositol polyphosphate 5-phosphatase, complete cds.
This hit is scoring at : 0.0 (expectation value)
Alignment length (overlap) : 621
Identities : 84 %
Scoring matrix : BLOSUM62 (used to infer consensus pattern)
Database searched : nrdb

```
Q: 131 RITVVTWNVGTAMPPDDVTSLLHLGGGDDSDGADMIAIGLQEVNSMLNKRLKDALFTDQW
       RITVVTWNVGTAMPPDDVTSLLHLGGG.DSDGADMIAIGLQEVNSM:NKRLKDALFTDQW
H: 419 RITVVTWNVGTAMPPDDVTSLLHLGGGHDSDGADMIAIGLQEVNSMINKRLKDALFTDQW

SELFMDALGPFNFVLVTHPSPPGQPETLLNSWLQLYPGSLWGPLGLCGWVSSVRMQGVIL
       SELFMDALGPFNFVLV                                  S:VRMQGVIL
       SELFMDALGPFNFVLV--------------------------------STVRMQGVIL

LLFAKYYHLPFLRDVQTDCTRTGLGGYWGNKGGVSVRLAAFGHMLCFLNCHLPAHMDKAE
       LLFAKYYHLPFLRDVQTDCTRTGLGGYWGNKGGVSVRLAAFGHMLCFLNCHLPAHMDKAE
       LLFAKYYHLPFLRDVQTDCTRTGLGGYWGNKGGVSVRLAAFGHMLCFLNCHLPAHMDKAE

QRKDNFQTILSLQQFQGPGAQGILDHEYGLGLVFWFGDLNFRIESYDLHFVKFAIDSDQL
       QRKDNFQTILSLQQFQGPGA.GILDH:         LVFWFGDLNFRIESYDLHFVKFAIDS:QL
       QRKDNFQTILSLQQFQGPGAHGILDHD----LVFWFGDLNFRIESYDLHFVKFAIDSNQL

HQLWEKDQLNMAKNTWPILKGFQEGPLNFAPTFKFDVGTNKYDTSAKKRKPAWTDRILWK
       HQLWEKDQLNMAKNTWPILKGFQEGPLNFAPTFKFDVGTNKYDTSAKKRKPAWTDRILWK
       HQLWEKDQLNMAKNTWPILKGFQEGPLNFAPTFKFDVGTNKYDTSAKKRKPAWTDRILWK
```

Fig. 13 (continued)

```
VKAPGGGPSPSGRKSHRLQVTQHSYRSHMEYTVSDHKPVAAQFLLQFAFRDDMPLVRLEV
VKAP.GGPSPSGR:SHRLQVTQHSYRSHMEYTVSDHKPVAA:FLLQFAFRDD:PLVRLEV
VKAPSGGPSPSGRESHRLQVTQHSYRSHMEYTVSDHKPVAARFLLQFAFRDDVPLVRLEV

ADEWVRPEQAVVRYRMETVFARSSWDWIGLYRVGFRHCKDYVAYVWAKHEDVDGNTYQVT
ADEW.RPEQAVVRYR:ETVFARSSWDWIGLYRVGFRHCKDYVAYVWAKHE:VDGN.YQVT
ADEWARPEQAVVRYRVETVFARSSWDWIGLYRVGFRHCKDYVAYVWAKHEEVDGNIYQVT

FSEESLPKGHGDFILGYYSHNHSILIGITEPFQIXLPXXELAXXXTDXXGTXXEGEDDXT
FSEESLPKGHGDFILGYYSH:HSILIG:TEPFQI.LP.E A...TD.GT..EGEDD.T
FSEESLPKGHGDFILGYYSHHHSILIGVTEPFQISLPTSESASSSTDSSGTSSEGEDDST

LELLAPKXRXPXPGKXKRHRXRXPGLARFPGLALRPXXRERRGAXRXPXPQXRRLXRVAP
LELLAPK.R.P.PGK.KRHR.R.PGLARFP.LALRP..RERRG..R.P.PQ.R:L RVAP
LELLAPKSRSPSPGKSKRHRSRSPGLARFPSLALRPSSRERRGGSRSPSPQSRQLPRVAP

DRXXNGXXRGXXEEGPXGLPGPWAFPPAVPRSLGLLPALRLETVDPGGGGSWGPDREALA
DR..:...RG..EEGP.G PGPWAFPPAVPRSLGLLPALRLETVDPGGGGSWGPD:EA
DRGHSSGSRGSSEEGPSGPPGPWAFPPAVPRSLGLLPALRLETVDPGGGGSWGPDQEAPD

PNSLSPSPQGHRGLEEGGLGP    751
PNSLSPSPQG. GLE:GGLGP
PNSLSPSPQGRLGLEDGGLGP   1001
```

Inositol polyphosphate phosphatase family in bold

Fig. 14

```
BLASTP - alignment of 249_genewise_pro against trembl|AB032551|AB032551_1
gene: "PIPP"; product: "proline-rich inositol polyphosphate 5-phosphatase";
Rattus norvegicus PIPP mRNA for proline-rich inositol polyphosphate 5-
phosphatase, complete cds. //:gp|AB032551|6906704 gene: "PIPP"; product:
"proline-rich inositol polyphosphate 5-phosphatase"; Rattus norvegicus PIPP
mRNA for proline-rich inositol polyphosphate 5-phosphatase, complete cds.
........
This hit is scoring at : 0.0 (expectation value)
Alignment length (overlap) : 1008
Identities : 83 %
Scoring matrix : BLOSUM62 (used to infer consensus pattern)
Database searched : nrdb_1_;

Q:  1 MEGQSSRGSRRPGTRAGLGSLPMPQGVAQTGAPSK-VDSSFQLPAKKNAALGPSEPRLAL
      MEGQS..GS.:.GTR.GLG.LP ..G..QTG.PSK V:SSFQLPAK N.. PSEPRLAL
H:  1 MEGQSRGSAKSGTRTGLGPLPGTHGALQTGTPSKKVNSSFQLPAK-NTGPTPSEPRLAL

APVGPRAAMSASSEGPRLALASPRPILAPLCTPEGQKTATAHRSSSLAPTSVGQLVMSAS
      APVGPRAA:S..SE PRLAL:SPRPILAPL.T.  QK....HRSS. APTSVGQLV:SA:
      APVGPRAAVSPPSERPRLALSSPRPILAPLSTAGEQKRPPHRSSKPAPTSVGQLVVSAA

AGPKPPPATTGSVLAPTSLG-LVMPASAGPRSPPVTLGPNLAPTSRDQKQEPPASVGPKP
      AGPKPPP..: S:LAP.SLG LV:.ASA PR..P..LGP L:PTSRDQKQ .P.SVGPKP
      AGPKPPPVASVSILAPKSLGLVISASAMPRPTPAPLGPILSPTSRDQKQLSPTSVGPKP

TLAASGLSLALASEEQPPELPSTPSPVPSPVLSPTQEQALAPASTASGAASVGQTSARKR
      .LA.SGLSLALAS:EQPP: PS:PSPVPSPVLSP:QE. LAPA...S .AS Q..AR::
      ALATSGLSLALASQEQPPQSPSSPSPVPSPVLSPSQESHLAPATVTSTPASERQLPARQK

DAPAPRPLPASEGHLQPPAQTSGPTGSPPCIQTSPDPRLSPSFRARPEALHSSPEDPVLP
      D.. RP:P.::G L..P.Q..G  SPP .QTS.DPRLSPSFRARPEA ..SPEDPVLP
      DTAVRRPIPPADGCLHTPVQAAGLATSPPRAQTSSDPRLSPSFRARPEAPRHSPEDPVLP
```

Fig. 14 (continued)

```
RPPQTLPLDVGQGPSEPGTHSPGLLSPTFRPGAPSGQTVPPPLPKPPRSPSPSHSPNR
PPQTLPLDV..G .E.GT.SPGLLSPTFRPG.PS.QTVPPPLPKPPRSPSRSPS.SPNR
PPPQTLPLDVSSGLPESGTRSPGLLSPTFRPGIPSNQTVPPPLPKPPRSPSRSPSRSPNR

SPCVPPAPDMALPRLGTQSTGPGRCLSPNLQAQEAPAPVTTSSSTSTLSSSPWSAQPTWK
SPCVPPAP::ALPR  TQ..GPG:C SPNLQ.QE:P...TS.::S   WSAQPT K
SPCVPPAPEVALPRPVTQGAGPGKCPSPNLQTQESPVATATSPTSS-----WSAQPTCK

SDPGFRITVVTWNVGTAMPPDDVTSLLHLGGGDDSDGADMIAIGLQEVNSMLNKRLKDAL
SDPGFRITVVTWNVGTAMPPDDVTSLLHLGGG..DSDGADMIAIGLQEVNSM:NKRLKDAL
SDPGFRITVVTWNVGTAMPPDDVTSLLHLGGGHDSDGADMIAIGLQEVNSMINKRLKDAL

FTDQWSELFMDALGPFNFVLVSSVRMQGVILLLFAKYYHLPFLRDVQTDCTRTGLGGYWG
FTDQWSELFMDALGPFNFVLVS:VRMQGVILLLFAKYYHLPFLRDVQTDCTRTGLGGYWG
FTDQWSELFMDALGPFNFVLVSTVRMQGVILLLFAKYYHLPFLRDVQTDCTRTGLGGYWG

NKGGVSVRLAAFGHMLCFLNCHLPAHMDKAEQRKDNFQTILSLQQFQGPGAQGILDHDLV
NKGGVSVRLAAFGHMLCFLNCHLPAHMDKAEQRKDNFQTILSLQQFQGPGA.GILDHDLV
NKGGVSVRLAAFGHMLCFLNCHLPAHMDKAEQRKDNFQTILSLQQFQGPGAHGILDHDLV

FWFGDLNFRIESYDLHFVKFAIDSDQLHQLWEKDQLNMAKNTWPILKGFQEGPLNFAPTF
FWFGDLNFRIESYDLHFVKFAIDS:QLHQLWEKDQLNMAKNTWPILKGFQEGPLNFAPTF
FWFGDLNFRIESYDLHFVKFAIDSNQLHQLWEKDQLNMAKNTWPILKGFQEGPLNFAPTF

KFDVGTNKYDTSAKKRKPAWTDRILWKVKAPGGGPSPSGRKSHRLQVTQHSYRSHMEYTV
KFDVGTNKYDTSAKKRKPAWTDRILWKVKAP.GGPSPSGR:SHRLQVTQHSYRSHMEYTV
KFDVGTNKYDTSAKKRKPAWTDRILWKVKAPSGGPSPSGRESHRLQVTQHSYRSHMEYTV

SDHKPVAAQFLLQFAFRDDMPLVRLEVADEWVRPEQAVVRYRMETVFARSSWDWIGLYRV
SDHKPVAA:FLLQFAFRDD:PLVRLEVADEW.RPEQAVVRYR.ETVFARSSWDWIGLYRV
SDHKPVAARFLLQFAFRDDVPLVRLEVADEWARPEQAVVRYRVETVFARSSWDWIGLYRV
```

Fig. 14 (continued)

```
GFRHCKDYVAYVWAKHEDVDGNTYQVTFSEESLPKGHGDFILGYYSHNHSILIGITEPFQ
GFRHCKDYVAYVWAKHE:VDGN.YQVTFSEESLPKGHGDFILGYYSH:HSILIG:TEPFQ
GFRHCKDYVAYVWAKHEEVDGNIYQVTFSEESLPKGHGDFILGYYSHHHSILIGVTEPFQ

ISLPSSELASSSTDSSGTSSEGEDDSTLELLAPKSRSPSPGKSKRHRSRSPGLARFPGLA
ISLP:SE ASSSTDSSGTSSEGEDDSTLELLAPKSRSPSPGKSKRHRSRSPGLARFP.LA
ISLPTSESASSSTDSSGTSSEGEDDSTLELLAPKSRSPSPGKSKRHRSRSPGLARFPSLA

LRPSSRERRGASRSPSPQSRRLSRVAPDRSSNGSSRGSSEEGPSGLPGPWAFPPAVPRSL
LRPSSRERRG.SRSPSPQSR:L.RVAPDR..:..SRGSSEEGPSG PGPWAFPPAVPRSL
LRPSSRERRGGSRSPSPQSRQLPRVAPDRGHSSGSRGSSEEGPSGPPGPWAFPPAVPRSL

GLLPALRLETVDPGGGGSWGPDREALAPNSLSPSPQGHRGLEEGGLGP     1006
GLLPALRLETVDPGGGGSWGPD:EA  PNSLSPSPQG. GLE:GGLGP
GLLPALRLETVDPGGGGSWGPDQEAPDPNSLSPSPQGRLGLEDGGLGP     1001
```

Fig. 15

```
HMMPFAM - alignment of 249 genewise pro against pfam|hmm|IPPc
Inositol polyphosphate phosphatase family, c
This hit is scoring at : 371.5
Scoring matrix : BLOSUM62 (used to infer consensus pattern)

Q: 421 PGFRITVTWNVGT-----AMPPDDVTSLLHLGGG------DDSDGADMIAIGLQEV---
        : :I V TWNVG       A.P.:D:TS L.             D::  .D:. .IGLQEV
H:   1 kdikifvgTWNVggrsfrskaspdtdltsWLfskadgtDeqkdteppDIyviGlQEvGGK -NKRLKDALFT
                                                          .D.L
       yessqVdiivkeLdAlkeyilqksvplnagNvfGaEDgPakWesLIRtLNtilnsdtlke -NSML------
        :L
       DQWSELFMDAL-----GPFNFVLVSSVRMQGVILLLFAKYYHLPFLRDVQTDCTRTGLGGY
       :W  .::L        :VL::S :: G:::LL:F.:   P.::DV:. .::.:TG:GGY
       reWlkeirkslnepstkskYvllaskqlvGilllVfvrknlrphikdvevstvktGiggy WGNKGGVSVRLAAFGH-----MLCFLNCHLPAHMD---KAEQRKDNFQTI-LSLQQFggPGAQ
       GNKGGV:VR.          CF:N.HL.A       .E:R.  .::I L.  :F P .:
       lGNKGgVavrfqlhdtwesfCFVnshLaAGeenlanverRnqDYkeIrlrrlrF..prgk G------------------ILDHDLVFWFGDLNFRIESYDL-------HFVKFAIDSDQ---LHQLW
                         I.DHD:VFW.GDLN:RIE   .:       V:  I          :L
                         ssdqrnfvagstIfdhDvvFWiGDLNyRielssvlvlvdtseevrelirkkdnryfdeLl EKDQLNMAKNTWPILKGFQEGPLNFAPTFKFD---VGTNKYDTSAKKRKPAWTDRILWKV
       EKDQL.   .  :KGF.EG..:.F.PT:K:D    GT:.YDTS.KKR PAW.DRILWK
       ekDQLkremkagkvFkgFtEgeitFpPTYkYdedypgtdnYdtsEKkRvPAWCDRILwks KAPggqpsPsgRKSHRLQVTQ--------HsYRSHMEYTVSDHKPVAAQFLLQF
       K.P.   R. L:.            Y S.ME:..SDHKPV.A.F :: .
       Krp....y..rtgpgleqlsesdldevitYtWPtl.YysrmeiktSDHkPVfAtFrvkv AFRD   736
         .D
       kvvd   414
```

ISOLATED HUMAN INOSITOL POLYPHOSPHATE 5-PHOSPHATASE

This application is a National Stage application of co-pending PCT application PCT/EP01/12496 filed Oct. 29, 2001, which was published in English under PCT Article 21(2) on May 10, 2002, which claims the benefit of U.S. provisional application Ser. No. 60/243,745 filed Oct. 30, 2000, Ser. No. 60/257,302 filed Dec. 26, 2000, and Ser. No. 60/314,660 filed Aug. 27, 2001. These applications are incorporated herein by reference in their entireties.

TECHNICAL FIELD OF THE INVENTION

The invention relates to the area of enzyme regulation. More particularly, the invention relates to the regulation of human inositol polyphosphate 5-phosphatase.

BACKGROUND OF THE INVENTION

SHC and GRB2 protein signaling molecules form a complex in response to growth factor or oncogenic transformation, as described in Rozakis-Adcock et al Nature 360: 689–92 (1992). U.S. Pat. No. 6,090,621. These proteins are thought to transmit mitogenic signals from receptor and non-receptor tyrosine kinases to ras, a member of a major class of oncogenes and proto-oncogenes that encode G proteins that are located on the inner face of the plasma membrane, where they bind and hydrolyze GTP. Ras proteins are involved in an unknown way in growth-factor stimulation of cell proliferation, as described in Alberts et al., *Molecular Biology of the Cell* (second edition, Garland publishing New York, 1989) pp. 699 and 705. The precise mechanism of the action of ras remains unknown, as indicated in Lowenstein et al Cell 70: 431–42 (1992) and Gale et al Nature 363: 88–92 (1993).

By expression interaction cloning, the GRB2 SH3 domains were found to bind to a GRB2-associated signaling inositol polyphosphate 5-phosphatase (called SIP-110), a 110 kDa protein believed to be involved in signaling events that follow growth factor stimulation, and occur between the cell surface and transcriptional activation events. Furthermore, SIP-110 is believed to participate in modulating signaling by ras and by phosphatidyl inositol 3-kinase (PI 3-kinase), two known regulators of cell growth. It would be advantageous in the process of elucidating the mechanism of ras, PI 3-kinase and other signaling molecules and pathways, to discover other signaling molecules that participate in the signal transduction that modulates the activity of the ras pathway, the PI 3-kinase pathway, the MAP kinase pathway, the calcium signaling pathway and other signaling pathways such that cellular responses including growth and proliferation may be regulated by regulating such signaling molecules.

Activation of phosphatidylinositol 3'-kinase (PI 3-kinase) by growth factors and oncogenes has been implicated as a critical step in mitogenic signaling and cellular transformation, as described in Cantley et al, Cell 64:281–302 (1991), Kapeller and Cantley. Bioessays 16:565–76 (1994), and Stephens et al, Biochim Biophys Acta 1179:27–75 (1993), PI 3-kinase consists of 85 kDa and 110 kDa subunits which associate with receptor tyrosine kinases and intracellular signaling molecules in response to treatment with growth factors or in transformed cells. Blockade of PI 3-kinase function either by mutagenesis or with pharmacological inhibitors prevents mitogenic signaling. Further, two products of PI 3-kinase, PtdIns(3,4,5)$P_3$ and PtdIns(3,4)$P_2$, increase in cells treated with mitogenic stimuli as Hawkins, et al. Nature 358:157–910, (1992) and Klippel et al, Molecular and Cellular Biology 16:41174127 (1996). The products of PI 3-kinase are presumed to act as second messengers or as regulators of protein-protein interactions. The regulation of PI 3-kinase activity during signaling is less well studied.

Changes in subcellular localization, in phosphorylation state and in conformation of the enzyme have been suggested to contribute to activation but little is known about how PI 3-kinase might be down-regulated. It would be advantageous to discover and characterize molecules implicated in PI 3-kinase mediated pathways, as a means to learning how to regulate PI 3-kinase. A number of distinct forms of inositol polyphosphate 5-phosphatase have been identified. Emeaux et al., *Biochim. Biophys. Acta* 1436, 185–99, 1998. There is, therefore, the possibility that additional forms of this enzyme exist which can be regulated to provide therapeutic effects.

SUMMARY OF THE INVENTION

It is an object of the invention to provide reagents and methods of regulating a human inositol polyphosphate 5-phosphatase. This and other objects of the invention are provided by one or more of the embodiments described below.

One embodiment of the invention is a inositol polyphosphate 5-phosphatase polypeptide comprising an amino acid sequence selected from the group consisting of:

amino acid sequences which are at least about 85% identical to the amino acid sequence shown in SEQ ID NO: 2;

the amino acid sequence shown in SEQ ID NO: 2;

amino acid sequences which are at least about 85% identical to the amino acid sequence shown in SEQ ID NO: 12; and the amino acid sequence shown in SEQ ID NO: 12.

Yet another embodiment of the invention is a method of screening for agents which decrease extracellular matrix degradation. A test compound is contacted with a inositol polyphosphate 5-phosphatase polypeptide comprising an amino acid sequence selected from the group consisting of:

amino acid sequences which are at least about 85% identical to the amino acid sequence shown in SEQ ID NO: 2;

the amino acid sequence shown in SEQ ID NO: 2;

amino acid sequences which are at least about 85% identical to the amino acid sequence shown in SEQ ID NO: 12; and the amino acid sequence shown in SEQ ID NO: 12.

Binding between the test compound and the inositol polyphosphate 5-phosphatase polypeptide is detected. A test compound which binds to the inositol polyphosphate 5-phosphatase polypeptide is thereby identified as a potential agent for decreasing extracellular matrix degradation. The agent can work by decreasing the activity of the inositol polyphosphate 5-phosphatase.

Another embodiment of the invention is a method of screening for agents which decrease extracellular matrix degradation. A test compound is contacted with a polynucleotide encoding a inositol polyphosphate 5-phosphatase polypeptide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 11; and the nucleotide sequence shown in SEQ ID NO: 11.

Binding of the test compound to the polynucleotide is detected. A test compound which binds to the polynucleotide is identified as a potential agent for decreasing extracellular matrix degradation. The agent can work by decreasing the amount of the inositol polyphosphate 5-phosphatase through interacting with the inositol polyphosphate 5-phosphatase mRNA.

Another embodiment of the invention is a method of screening for agents which regulate extracellular matrix degradation. A test compound is contacted with a inositol polyphosphate 5-phosphatase polypeptide comprising an amino acid sequence selected from the group consisting of:

amino acid sequences which are at least about 85% identical to the amino acid sequence shown in SEQ ID NO: 2;

the amino acid sequence shown in SEQ ID NO: 2;

amino acid sequences which are at least about 85% identical to the amino acid sequence shown in SEQ ID NO: 12; and the amino acid sequence shown in SEQ ID NO:12.

A inositol polyphosphate 5-phosphatase activity of the polypeptide is detected. A test compound which increases inositol polyphosphate 5-phosphatase activity of the polypeptide relative to inositol polyphosphate 5-phosphatase activity in the absence of the test compound is thereby identified as a potential agent for increasing extracellular matrix degradation. A test compound which decreases inositol polyphosphate 5-phosphatase activity of the polypeptide relative to inositol polyphosphate 5-phosphatase activity in the absence of the test compound is thereby identified as a potential agent for decreasing extracellular matrix degradation.

Even another embodiment of the invention is a method of screening for agents which decrease extracellular matrix degradation. A test compound is contacted with a inositol polyphosphate 5-phosphatase product of a polynucleotide which comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 11; and the nucleotide sequence shown in SEQ ID NO: 11.

Binding of the test compound to the inositol polyphosphate 5-phosphatase product is detected. A test compound which binds to the inositol polyphosphate 5-phosphatase product is thereby identified as a potential agent for decreasing extracellular matrix degradation.

Still another embodiment of the invention is a method of reducing extracellular matrix degradation. A cell is contacted with a reagent which specifically binds to a polynucleotide encoding a inositol polyphosphate 5-phosphatase polypeptide or the product encoded by the polynucleotide, wherein the polynucleotide comprises a nucleotide sequence selected from the group consisting of:

nucleotide sequences which are at least about 50% identical to the nucleotide sequence shown in SEQ ID NO: 1;

the nucleotide sequence shown in SEQ ID NO: 1;

nucleotide sequences which are at least about 50% identical to the nucleotide sequence shown in SEQ ID NO: 11; and the nucleotide sequence shown in SEQ ID NO: 11.

Inositol polyphosphate 5-phosphatase activity in the cell is thereby decreased.

The invention thus provides a human inositol polyphosphate 5-phosphatase which can be used to identify test compounds which may act, for example, as activators or inhibitors at the enzyme's active site. Human inositol polyphosphate 5-phosphatase and fragments thereof also are useful in raising specific antibodies which can block the enzyme and effectively reduce its activity.

BRIEF DESCRIPTION OF THE DRAWINGS

FIG. 1 shows the DNA-sequence encoding a inositol polyphosphate 5-phosphatase Polypeptide (SEQ ID NO: 1).

FIG. 2 shows the amino acid sequence deduced from the DNA-sequence of FIG. 1 (SEQ ID NO: 2).

FIG. 3 shows the amino acid sequence of the protein identified by trembl Accession No. AB032551 (SEQ ID NO: 3).

FIG. 4 shows the DNA-sequence encoding a inositol polyphosphate 5-phosphatase Polypeptide (SEQ ID NO: 4).

FIG. 5 shows the DNA-sequence encoding a inositol polyphosphate 5-phosphatase Polypeptide (SEQ ID NO: 5).

FIG. 6 shows the DNA-sequence encoding a inositol polyphosphate 5-phosphatase Polypeptide (SEQ ID NO: 6).

FIG. 7 shows the DNA-sequence encoding a inositol polyphosphate 5-phosphatase Polypeptide (SEQ ID NO: 7).

FIG. 8 shows the DNA-sequence encoding a inositol polyphosphate 5-phosphatase Polypeptide (SEQ ID NO:8).

FIG. 9 shows the DNA-sequence encoding a inositol polyphosphate 5-phosphatase Polypeptide (SEQ ID NO: 9).

FIG. 10 shows the DNA-sequence encoding a inositol polyphosphate 5-phosphatase Polypeptide (SEQ ID NO: 10).

FIG. 11 shows the DNA-sequence encoding a inositol polyphosphate 5-phosphatase Polypeptide (SEQ ID NO: 11).

FIG. 12 shows the amino acid sequence deduced from the DNA-sequence of FIG. 11 (SEQ ID NO: 12).

FIG. 13 shows the BLASTP alignment of human inositol polyphosphate 5-phosphatase (SEQ ID NO: 2) with the protein identified with trembl Accession No. AB032551 (SEQ ID NO: 3).

FIG. 14 shows the BLASTP—alignment of 249_genewise_pro (SEQ ID NO: 12) against trembl|AB032551|AB032551_1(SEQ ID NO: 3).

FIG. 15 shows the HMMPFAM—alignment of 249_genewise_pro (SEQ ID NO: 12) against pfam|hmm|IPPc (Inositol polyphosphate phosphatase family, c).

Figure 16:
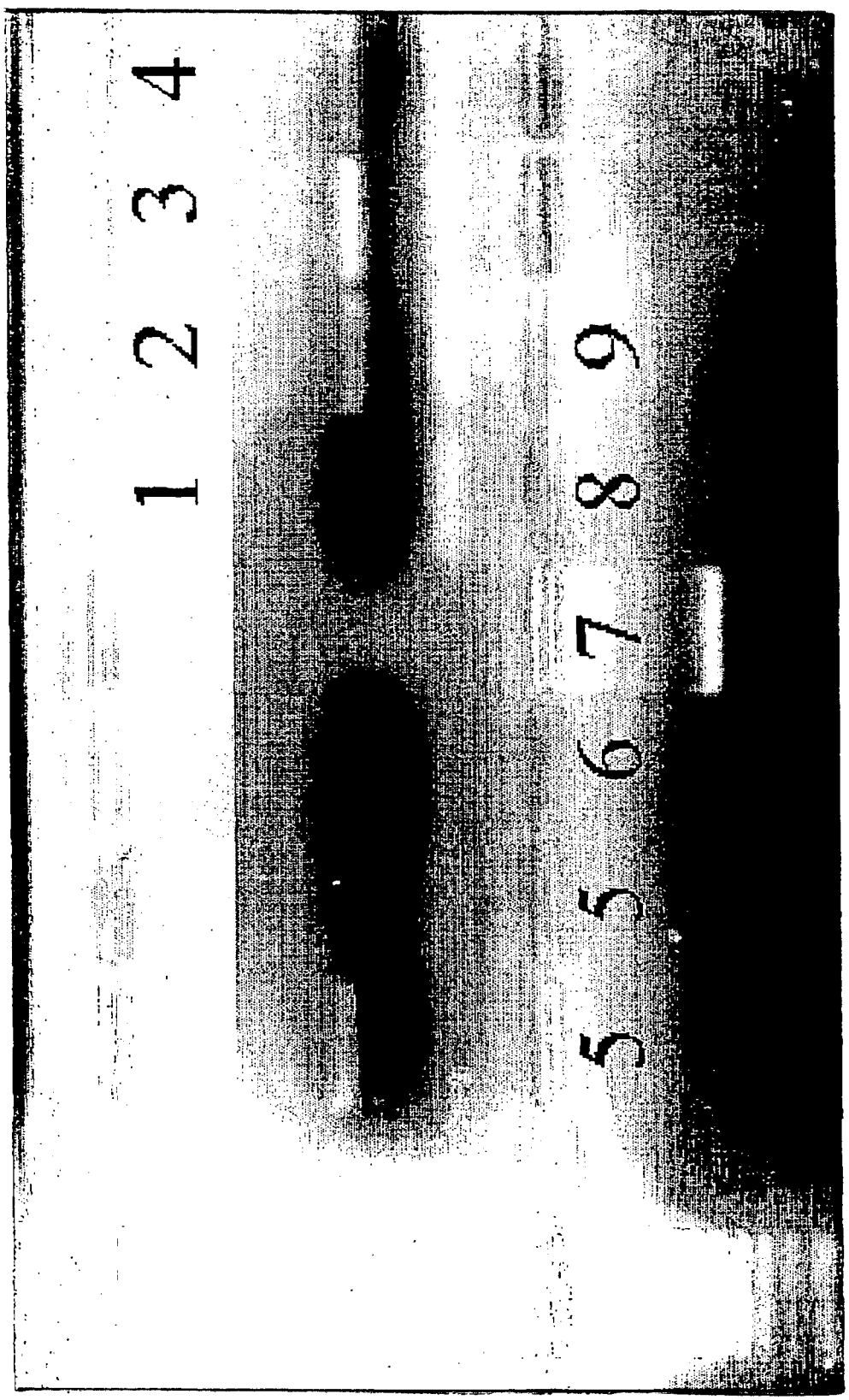
FIG. 16 shows the gene expression of human inositol polyphosphate 5-phosphatase in human tissues relevant for diabetes and obesity as determined by RT-PCR with 35 cycles performed with gene specific primers according to a standard procedure as known in the art (described e.g. in EXAMPLE 6).

The following tissues are represented: Lane 1-Liver, lane 2-Skeletal Muscle, lane 3-Hypothalamus, lane 4-Islets, lane 5-Adipose Sub., lane 6-Adipose Mes., lane 7-Genomic DNA, lane 8-No amplification conrtol and, lane 9-No template control. Expression is shown in lanes 2, 3 and 4.

DETAILED DESCRIPTION OF THE INVENTION

The invention relates to an isolated polynucleotide encoding a inositol polyphosphate 5-phosphatase polypeptide and being selected from the group consisting of:

a) a polynucleotide encoding a inositol polyphosphate 5-phosphatase polypeptide comprising an amino acid sequence selected from the group consisting of:
   amino acid sequences which are at least about 85% identical to the amino acid sequence shown in SEQ ID NO: 2;
   the amino acid sequence shown in SEQ ID NO: 2;
   amino acid sequences which are at least about 85% identical to the amino acid sequence shown in SEQ ID NO: 12; and
   the amino acid sequence shown in SEQ ID NO: 12.
b) a polynucleotide comprising the sequence of SEQ ID NOS: 1 or 11;
c) a polynucleotide which hybridizes under stringent conditions to a polynucleotide specified in (a) and (b);
d) a polynucleotide the sequence of which deviates from the polynucleotide sequences specified in (a) to (c) due to the degeneration of the genetic code; and
e) a polynucleotide which represents a fragment, derivative or allelic variation of a polynucleotide sequence specified in (a) to (d).

Furthermore, it has been discovered by the present applicant that a novel inositol polyphosphate 5-phosphatase, particularly a human inositol polyphosphate 5-phosphatase, is a discovery of the present invention. Human inositol polyphosphate 5-phosphatase comprises the amino acid sequence shown in SEQ ID NOS: 2 AND 12. A coding sequence for human inositol polyphosphate 5-phosphatase is shown in SEQ ID NOS: 1 AND 11. Related ESTs (SEQ ID NOS: 4–10) are expressed in head and neck, whole brain, infant brain, kidney, uterus, thyroid tumor, and mammary gland. Known inositol polyphosphate 5-phosphatases have been detected in lung, thymus, testes, placenta, heart, brain, kidney, ovary, and colon. Speed et al., *Eur. J. Biochem.* 234, 216–24, 1995; Kudo et al., *Brain Res. Mol. Brain Res.* 75, 172–77, 2000. Inositol polyphosphate 5-phosphatase also has been detected in membrane ruffles. Mochizuki & Takenawa, *J. Biol. Chem.* 274, 36790–95, 1999.

Human inositol polyphosphate 5-phosphatase is 84% identical over 621 amino acids to the protein identified with trembl Accession No. AB032551 and annotated as "proline-rich inositol polyphosphate 5-phosphatase" (FIG. 13).

Human inositol polyphosphate 5-phosphatase of the invention is expected to be useful for the same purposes as previously identified inositol polyphosphate 5-phosphatase enzymes. Human inositol polyphosphate 5-phosphatase is believed to be useful in therapeutic methods to treat disorders such as COPD, asthma, diabetes, and cancer. Human inositol polyphosphate 5-phosphatase also can be used to screen for human inositol polyphosphate 5-phosphatase activators and inhibitors.

Polypeptides

Human inositol polyphosphate 5-phosphatase polypeptides according to the invention comprise at least 6, 10, 15, 20, 25, 50, 75, 100, 125, 150, 175, 200, 250, 300, 350, 400, 450, 500, 550, 600, 650, 700, or 750 contiguous amino acids selected from the amino acid sequence shown in SEQ ID NOS:2 AND 12 or a biologically active variant thereof, as defined below. A inositol polyphosphate 5-phosphatase polypeptide of the invention therefore can be a portion of a inositol polyphosphate 5-phosphatase protein, a full-length inositol polyphosphate 5-phosphatase protein, or a fusion protein comprising all or a portion of a inositol polyphosphate 5-phosphatase protein.

Biologically Active Variants

Human inositol polyphosphate 5-phosphatase polypeptide variants which are biologically active, e.g., retain an inositol polyphosphate 5-phosphatase activity, also are inositol polyphosphate 5-phosphatase polypeptides. Preferably, naturally or non-naturally occurring inositol polyphosphate 5-phosphatase polypeptide variants have amino acid sequences which are at least about 85, 90, 96, 96, or 98% identical to the amino acid sequence shown in SEQ ID NOS: 2 AND 12 or a fragment thereof. Percent identity between a putative inositol polyphosphate 5-phosphatase polypeptide variant and an amino acid sequence of SEQ ID NOS: 2 AND 12 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a inositol polyphosphate 5-phosphatase polypeptide can be found using computer programs well known in the art, such as DNASTAR software. Whether an amino acid change results in a biologically active inositol polyphosphate 5-phosphatase polypeptide can readily be determined by assaying for inositol polyphosphate 5-phosphatase activity, as described for example, in U.S. Pat. No. 6,090,621.

Fusion Proteins

Fusion proteins are useful for generating antibodies against inositol polyphosphate 5-phosphatase polypeptide amino acid sequences and for use in various assay systems. For example, fusion proteins can be used to identify proteins which interact with portions of a inositol polyphosphate 5-phosphatase polypeptide. Protein affinity chromatography or library-based assays for protein-protein interactions, such as the yeast two-hybrid or phage display systems, can be used for this purpose. Such methods are well known in the art and also can be used as drug screens.

A inositol polyphosphate 5-phosphatase polypeptide fusion protein comprises two polypeptide segments fused together by means of a peptide bond. The first polypeptide segment comprises at least 6, 10, 15, 20, 25, 50, 75, 100, 125, 150, 175, 200, 250, 300, 350, 400, 450, 500, 550, 600, 650, 700, or 750 contiguous amino acids of SEQ ID NOS:2 AND 12 or of a biologically active variant, such as those described above. The first polypeptide segment also can comprise full-length inositol polyphosphate 5-phosphatase protein.

The second polypeptide segment can be a full-length protein or a protein fragment. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the inositol polyphosphate 5-phosphatase polypeptide-encoding sequence and the heterologous protein sequence, so that the inositol polyphosphate 5-phosphatase polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from the complement of SEQ ID NOS: 1 AND 11 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz BioTechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human inositol polyphosphate 5-phosphatase polypeptide can be obtained using inositol polyphosphate 5-phosphatase polypeptide polynucleotides (described below) to make suitable probes or primers for screening cDNA expression libraries from other species, such as mice, monkeys, or yeast, identifying cDNAs which encode homologs of inositol polyphosphate 5-phosphatase polypeptide, and expressing the cDNAs as is known in the art.

Polynucleotides

A inositol polyphosphate 5-phosphatase polynucleotide can be single- or double-stranded and comprises a coding sequence or the complement of a coding sequence for a inositol polyphosphate 5-phosphatase polypeptide. A coding sequence for human inositol polyphosphate 5-phosphatase is shown in SEQ ID NOS: 1 AND 11.

Degenerate nucleotide sequences encoding human inositol polyphosphate 5-phosphatase polypeptides, as well as homologous nucleotide sequences which are at least about 50, 55, 60, 65, 70, preferably about 75, 90, 96, or 98% identical to the nucleotide sequence shown in SEQ ID NOS: 1 AND 11 or its complement also are inositol polyphosphate 5-phosphatase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of inositol polyphosphate 5-phosphatase polynucleotides which encode biologically active inositol polyphosphate 5-phosphatase polypeptides also are inositol polyphosphate 5-phosphatase polynucleotides. Polynucleotides comprising at least 6, 7, 8, 9, 10, 12, 15, 18, 20, or 25 contiguous nucleotides of SEQ ID NOS: 1 AND 11 or its complement also are human inositol polyphosphate 5-phosphatase polynucleotides. Such polynucleotides can be used, for example, as hybridization probes or antisense oligonucleotides.

Identification of Polynucleotide Variants and Homologs

Variants and homologs of the inositol polyphosphate 5-phosphatase polynucleotides described above also are inositol polyphosphate 5-phosphatase polynucleotides. Typically, homologous inositol polyphosphate 5-phosphatase polynucleotide sequences can be identified by hybridization of candidate polynucleotides to known inositol polyphosphate 5-phosphatase polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the inositol polyphosphate 5-phosphatase polynucleotides disclosed herein also can be identified by making suitable probes or primers and screening cDNA expression libraries from other species, such as mice, monkeys, or yeast. Human variants of inositol polyphosphate 5-phosphatase polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human inositol polyphosphate 5-phosphatase polynucleotides or inositol polyphosphate 5-phosphatase polynucleotides of other species can therefore be identified by hybridizing a putative homologous inositol polyphosphate 5-phosphatase polynucleotide with a polynucleotide having a nucleotide sequence of SEQ ID NOS: 1 AND 11 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to inositol polyphosphate 5-phosphatase polynucleotides or their complements following stringent hybridization and/or wash conditions also are inositol polyphosphate 5-phosphatase polynucleotides. Stringent wash conditions are well known and understood in the art and are disclosed, for example, in Sambrook et al., *Molecular Cloning: A Laboratory Manual*, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a inositol polyphosphate 5-phosphatase polynucleotide having a nucleotide sequence shown in SEQ ID NOS:1 AND 11 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% \text{ G+C}) - 0.63(\% \text{ formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A inositol polyphosphate 5-phosphatase polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated inositol polyphosphate 5-phosphatase polynucleotides. For example, restriction enzymes and probes can be used to isolate polynucleotide fragments which comprises inositol polyphosphate 5-phosphatase nucleotide sequences. Isolated polynucleotides are in preparations which are free or at least 70, 80, or 90% free of other molecules.

Human inositol polyphosphate 5-phosphatase cDNA molecules can be made with standard molecular biology techniques, using inositol polyphosphate 5-phosphatase mRNA as a template. Human inositol polyphosphate 5-phosphatase cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesizes inositol polyphosphate 5-phosphatase polynucleotides. The degeneracy of the genetic code allows alternate nucleotide sequences to be synthesized which will encode a inositol polyphosphate 5-phosphatase polypeptide having, for example, an amino acid sequence shown in SEQ ID NOS: 1 AND 11 or a biologically active variant thereof.

Extending Polynucleotides

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif.) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5'regions of genes. Use of a randomly primed library may be especially preferable for situations in which an oligo d(T) library does not yield a full-length cDNA. Genomic libraries can be useful for extension of sequence into 5'non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

Human inositol polyphosphate 5-phosphatase polypeptides can be obtained, for example, by purification from human cells, by expression of inositol polyphosphate 5-phosphatase polynucleotides, or by direct chemical synthesis.

Protein Purification

Human inositol polyphosphate 5-phosphatase polypeptides can be purified from any cell which expresses the enzyme, including host cells which have been transfected with inositol polyphosphate 5-phosphatase expression constructs. A purified inositol polyphosphate 5-phosphatase polypeptide is separated from other compounds which normally associate with the inositol polyphosphate 5-phosphatase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified inositol polyphosphate 5-phosphatase polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a inositol polyphosphate 5-phosphatase polynucleotide, the polynucleotide can be inserted into an expression vector which contains the necessary elements for the transcription and translation of the inserted coding sequence. Methods which are well known to those skilled in the art can be used to construct expression vectors containing sequences encoding inositol polyphosphate 5-phosphatase polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., *Current Protocols in Molecular Biology*, John Wiley & Sons, New York, N.Y., 1989.

A variety of expression vector/host systems can be utilized to contain and express sequences encoding a inositol polyphosphate 5-phosphatase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a inositol polyphosphate 5-phosphatase polypeptide, vectors based on SV40 or EBV can be used with an appropriate selectable marker.

Bacterial and Yeast Expression Systems

In bacterial systems, a number of expression vectors can be selected depending upon the use intended for the inositol polyphosphate 5-phosphatase polypeptide. For example, when a large quantity of a inositol polyphosphate 5-phosphatase polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the inositol polyphosphate 5-phosphatase polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding inositol polyphosphate 5-phosphatase polypeptides can be driven by any of a number of promoters. For example, viral promoters such as the 35S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in McGRAW HILL *Yearbook of Science and Technology*, McGraw Hill, New York, N.Y., pp. 191–196, 1992).

An insect system also can be used to express a inositol polyphosphate 5-phosphatase polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding inositol polyphosphate 5-phosphatase polypeptides can be cloned into a non-essential region of the virus, such as the polyhedrin gene, and placed under control of the polyhedrin promoter. Successful insertion of inositol polyphosphate 5-phosphatase polypeptides will render the polyhedrin gene inactive and produce recombinant virus lacking coat protein. The recombinant viruses can then be used to infect *S. frugiperda* cells or *Trichoplusia* larvae in which inositol polyphosphate 5-phosphatase polypeptides can be expressed (Engelhard et al., *Proc. Nat. Acad. Sci.* 91, 3224–3227, 1994).

Mammalian Expression Systems

A number of viral-based expression systems can be used to express inositol polyphosphate 5-phosphatase polypeptides in mammalian host cells. For example, if an adenovirus is used as an expression vector, sequences encoding inositol polyphosphate 5-phosphatase polypeptides can be ligated into an adenovirus transcription/translation complex comprising the late promoter and tripartite leader sequence. Insertion in a non-essential E1 or E3 region of the viral genome can be used to obtain a viable virus which is capable of expressing a inositol polyphosphate 5-phosphatase polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding inositol polyphosphate 5-phosphatase polypeptides. Such signals include the ATG initiation codon and adjacent sequences. In cases where sequences encoding a inositol polyphosphate 5-phosphatase polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., Results Probl. Cell Differ. 20, 125–162, 1994).

Host Cells

A host cell strain can be chosen for its ability to modulate the expression of the inserted sequences or to process the expressed inositol polyphosphate 5-phosphatase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110–2209) and can be chosen to ensure the correct modification and processing of the foreign protein.

Stable expression is preferred for long-term, high-yield production of recombinant proteins. For example, cell lines which stably express inositol polyphosphate 5-phosphatase polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced inositol polyphosphate 5-phosphatase sequences. Resistant clones of stably transformed cells can be proliferated using tissue culture techniques appropriate to the cell type. See, for example, Animal Cell Culture, R. I. Freshney, ed., 1986.

Any number of selection systems can be used to recover transformed cell lines.

These include, but are not limited to, the herpes simplex virus thymidine kinase (Wigler et al., Cell 11, 223–32, 1977) and adenine phosphoribosyltransferase (Lowy et al., Cell 22, 817–23, 1980) genes which can be employed in tk$^{31}$ or aprt$^-$ cells, respectively. Also, antimetabolite, antibiotic, or herbicide resistance can be used as the basis for selection. For example, dhfr confers resistance to methotrexate (Wigler et al., Proc. Natl. Acad. Sci. 77, 3567–70, 1980), npt confers resistance to the aminoglycosides, neomycin and G418 (Colbere-Garapin et al., J. Mol. Biol. 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, Proc. Natl. Acad. Sci. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., Methods Mol. Biol. 55, 121–131, 1995).

Detecting Expression

Although the presence of marker gene expression suggests that the inositol polyphosphate 5-phosphatase polynucleotide is also present, its presence and expression may need to be confirmed. For example, if a sequence encoding a inositol polyphosphate 5-phosphatase polypeptide is inserted within a marker gene sequence, transformed cells containing sequences which encode a inositol polyphosphate 5-phosphatase polypeptide can be identified by the absence of marker gene function. Alternatively, a marker gene can be placed in tandem with a sequence encoding a inositol polyphosphate 5-phosphatase polypeptide under the control of a single promoter. Expression of the marker gene in response to induction or selection usually indicates expression of the inositol polyphosphate 5-phosphatase polynucleotide.

Alternatively, host cells which contain a inositol polyphosphate 5-phosphatase polynucleotide and which express a inositol polyphosphate 5-phosphatase polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein. For example, the presence of a polynucleotide sequence encoding a inositol polyphosphate 5-phosphatase polypeptide can be detected by DNA-DNA or DNA-RNA hybridization or amplification using probes or fragments or fragments of polynucleotides encoding a inositol polyphosphate 5-phosphatase polypeptide. Nucleic acid amplification-based assays involve the use of oligonucleotides selected from sequences encoding a inositol polyphosphate 5-phosphatase polypeptide to detect transformants which contain a inositol polyphosphate 5-phosphatase polynucleotide.

A variety of protocols for detecting and measuring the expression of a inositol polyphosphate 5-phosphatase polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a inositol polyphosphate 5-phosphatase polypeptide can be used, or a competitive binding assay can be employed. These and other assays are described in Hampton et al., Serological Methods: A Laboratory Manual, APS Press, St. Paul, Minn., 1990) and Maddox et al., J. Exp. Med. 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding inositol polyphosphate 5-phosphatase polypeptides include oligolabeling, nick translation, end-labeling, or PCR amplification using a labeled nucleotide. Alternatively, sequences encoding a inositol polyphosphate 5-phosphatase polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a inositol polyphosphate 5-phosphatase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode inositol polyphosphate 5-phosphatase polypeptides can be designed to contain signal sequences which direct secretion of soluble inositol polyphosphate 5-phosphatase polypeptides through a prokaryotic or eukaryotic cell membrane or which direct the membrane insertion of membrane-bound inositol polyphosphate 5-phosphatase polypeptide.

As discussed above, other constructions can be used to join a sequence encoding a inositol polyphosphate 5-phosphatase polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the inositol polyphosphate 5-phosphatase polypeptide also can be used to facilitate purification. One such expression vector provides for expression of a fusion protein containing a inositol polyphosphate 5-phosphatase polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the _inositol polyphosphate 5-phosphatase polypeptide from the fusion protein. Vectors which contain fusion proteins are disclosed in Kroll et al., *DNA Cell Biol.* 12, 441–453, 1993.

Chemical Synthesis

Sequences encoding a inositol polyphosphate 5-phosphatase polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a inositol polyphosphate 5-phosphatase polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of inositol polyphosphate 5-phosphatase polypeptides can be separately synthesized and combined using chemical methods to produce a full-length molecule.

The newly synthesized peptide can be substantially purified by preparative high performance liquid chromatography (e.g., Creighton, *PROTEINS: Structures and Molecular Principles*, W H Freeman and Co., New York, N.Y., 1983). The composition of a synthetic inositol polyphosphate 5-phosphatase polypeptide can be confirmed by amino acid analysis or sequencing (e.g., the Edman degradation procedure; see Creighton, supra). Additionally, any portion of the amino acid sequence of the inositol polyphosphate 5-phosphatase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce inositol polyphosphate 5-phosphatase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter inositol polyphosphate 5-phosphatase polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a inositol polyphosphate 5-phosphatase polypeptide. "Antibody" as used herein includes intact immunoglobulin molecules, as well as fragments thereof, such as Fab, F(ab')$_2$, and Fv, which are capable of binding an epitope of a inositol polyphosphate 5-phosphatase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a inositol polyphosphate 5-phosphatase polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen.

Typically, an antibody which specifically binds to a inositol polyphosphate 5-phosphatase polypeptide provides a detection signal at least 5-, 10-, or 20-fold higher than a detection signal provided with other proteins when used in an immunochemical assay. Preferably, antibodies which specifically bind to inositol polyphosphate 5-phosphatase polypeptides do not detect other proteins in immunochemical assays and can immunoprecipitate a inositol polyphosphate 5-phosphatase polypeptide from solution.

Human inositol polyphosphate 5-phosphatase polypeptides can be used to immunize a mammal, such as a mouse, rat, rabbit, guinea pig, monkey, or human, to produce polyclonal antibodies. If desired, a inositol polyphosphate 5-phosphatase polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies which specifically bind to a inositol polyphosphate 5-phosphatase polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies which specifically bind to a inositol polyphosphate 5-phosphatase polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to inositol polyphosphate 5-phosphatase polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to inositol polyphosphate 5-phosphatase polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a inositol polyphosphate 5-phosphatase polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of inositol polyphosphate 5-phosphatase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583, 1990.

Modifications of inositol polyphosphate 5-phosphatase gene expression can be obtained by designing antisense oligonucleotides which will form duplexes to the control, 5', or regulatory regions of the inositol polyphosphate 5-phosphatase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, *Molecular and Immunologic Approaches*, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a inositol polyphosphate 5-phosphatase polynucleotide. Antisense oligonucleotides which comprise, for example, 2, 3, 4, or 5 or more stretches of contiguous nucleotides which are precisely complementary to a inositol polyphosphate 5-phosphatase polynucleotide, each separated by a stretch of contiguous nucleotides which are not complementary to adjacent inositol polyphosphate 5-phosphatase nucleotides, can provide sufficient targeting specificity for inositol polyphosphate 5-phosphatase mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular inositol polyphosphate 5-phosphatase polynucleotide sequence.

Antisense oligonucleotides can be modified without affecting their ability to hybridize to a inositol polyphosphate 5-phosphatase polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a inositol polyphosphate 5-phosphatase polynucleotide can be used to generate ribozymes which will specifically bind to mRNA transcribed from the inositol polyphosphate 5-phosphatase polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a inositol polyphosphate 5-phosphatase RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate inositol polyphosphate 5-phosphatase RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease inositol polyphosphate 5-phosphatase expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human inositol polyphosphate 5-phosphatase. Such genes may represent genes which are differentially expressed in disorders including, but not limited to, cancer, COPD, diabetes, and asthma. Further, such genes may represent genes which are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human inositol polyphosphate 5-phosphatase gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique which does not select against the isolation of mRNA may be utilized for the purification of such RNA samples. See, for example, Ausubel et al., ed., Current Protocols in Molecular Biology, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples which represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., *Nature* 308, 149–53; Lee et al., *Proc. Natl. Acad. Sci. U.S.A.* 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human inositol polyphosphate 5-phosphatase. For example, treatment may include a modulation of expression of the differentially expressed genes and/or the gene encoding the human inositol polyphosphate 5-phosphatase. The differential expression information may indicate whether the expression or activity of the differentially expressed gene or gene product or the human inositol polyphosphate 5-phosphatase gene or gene product are up-regulated or down-regulated.

Screening Methods

The invention provides assays for screening test compounds which bind to or modulate the activity of a inositol polyphosphate 5-phosphatase polypeptide or a inositol polyphosphate 5-phosphatase polynucleotide. A test compound preferably binds to a inositol polyphosphate 5-phosphatase polypeptide or polynucleotide. More preferably, a test compound decreases or increases an inositol polyphosphate 5-phosphatase activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.A.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412–421, 1992), or on beads (Lam, *Nature* 354, 82–84, 1991), chips (Fodor, *Nature* 364, 555–556, 1993), bacteria or spores (Ladner, U.S. Pat. No. 5,223,409), plasmids (Cull et al., *Proc. Natl. Acad. Sci. U.S.A.* 89, 1865–1869, 1992), or phage (Scott & Smith, *Science* 249, 386–390, 1990; Devlin, *Science* 249, 404–406, 1990); Cwirla et al., *Proc. Natl. Acad. Sci.* 97, 6378–6382, 1990; Felici, *J. Mol. Biol.* 222, 301–310, 1991; and Ladner, U.S. Pat. No. 5,223,409).

High Throughput Screening

Test compounds can be screened for the ability to bind to inositol polyphosphate 5-phosphatase polypeptides or polynucleotides or to affect inositol polyphosphate 5-phosphatase activity or inositol polyphosphate 5-phosphatase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies, for example, the active site of the inositol polyphosphate 5-phosphatase polypeptide, such that normal biological activity is prevented. Examples of such small molecules include, but are not limited to, small peptides or peptide-like molecules.

In binding assays, either the test compound or the inositol polyphosphate 5-phosphatase polypeptide can comprise a detectable label, such as a fluorescent, radioisotopic, chemiluminescent, or enzymatic label, such as horseradish peroxidase, alkaline phosphatase, or luciferase. Detection of a test compound which is bound to the inositol polyphosphate 5-phosphatase polypeptide can then be accomplished, for example, by direct counting of radioemission, by scintillation counting, or by determining conversion of an appropriate substrate to a detectable product.

Alternatively, binding of a test compound to a inositol polyphosphate 5-phosphatase polypeptide can be determined without labeling either of the interactants. For example, a microphysiometer can be used to detect binding of a test compound with a inositol polyphosphate 5-phosphatase polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a inositol polyphosphate 5-phosphatase polypeptide (McConnell et al., *Science* 257, 1906–1912, 1992).

Determining the ability of a test compound to bind to a inositol polyphosphate 5-phosphatase polypeptide also can be accomplished using a technology such as real-time Bimolecular Interaction Analysis (BIA) (Sjolander & Urbaniczky, *Anal. Chem.* 63, 2338–2345, 1991, and Szabo et al., *Curr. Opin. Struct. Biol.* 5, 699–705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a inositol polyphosphate 5-phosphatase polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent WO94/10300), to identify other proteins which bind to or interact with the inositol polyphosphate 5-phosphatase polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a inositol polyphosphate 5-phosphatase polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the inositol polyphosphate 5-phosphatase polypeptide.

It may be desirable to immobilize either the inositol polyphosphate 5-phosphatase polypeptide (or polynucleotide) or the test compound to facilitate separation of bound from unbound forms of one or both of the interactants, as well as to accommodate automation of the assay. Thus, either the inositol polyphosphate 5-phosphatase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a inositol polyphosphate 5-phosphatase polypeptide (or polynucleotide) can be accomplished in any vessel suitable for containing the reactants. Examples of such vessels include microtiter plates, test tubes, and microcentrifuge tubes.

In one embodiment, the inositol polyphosphate 5-phosphatase polypeptide is a fusion protein comprising a domain that allows the inositol polyphosphate 5-phosphatase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed inositol polyphosphate 5-phosphatase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a inositol polyphosphate 5-phosphatase polypeptide (or polynucleotide) or a test compound can be immobilized utilizing conjugation of biotin and streptavidin. Biotinylated inositol polyphosphate 5-phosphatase polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a inositol polyphosphate 5-phosphatase polypeptide, polynucleotide, or a test compound, but which do not interfere with a desired binding site, such as the active site of the inositol polyphosphate 5-phosphatase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antbodies which specifically bind to the inositol polyphosphate 5-phosphatase polypeptide or test compound, enzyme-linked assays which rely on detecting an activity of the inositol polyphosphate 5-phosphatase polypeptide, and SDS gel electrophoresis under non-reducing conditions.

Screening for test compounds which bind to a inositol polyphosphate 5-phosphatase polypeptide or polynucleotide also can be carried out in an intact cell. Any cell which comprises a inositol polyphosphate 5-phosphatase polypeptide or polynucleotide can be used in a cell-based assay system. A inositol polyphosphate 5-phosphatase polynucleotide can be naturally occurring in the cell or can be introduced using techniques such as those described above. Binding of the test compound to a inositol polyphosphate 5-phosphatase polypeptide or polynucleotide is determined as described above.

Enzyme Assays

Test compounds can be tested for the ability to increase or decrease the enzyme activity of a human inositol polyphosphate 5-phosphatase polypeptide. Enzyme activity can be measured, for example, as described in U.S. Pat. No. 6,090,621.

Enzyme assays can be carried out after contacting either a purified inositol polyphosphate 5-phosphatase polypeptide, a cell membrane preparation, or an intact cell with a test compound. A test compound which decreases an enzyme activity of a inositol polyphosphate 5-phosphatase polypeptide by at least about 10, preferably about 50, more preferably about 75, 90, or 100% is identified as a potential therapeutic agent for decreasing inositol polyphosphate 5-phosphatase activity. A test compound which increases an enzyme activity of a human inositol polyphosphate 5-phosphatase polypeptide by at least about 10, preferably about 50, more preferably about 75, 90, or 100% is identified as a potential therapeutic agent for increasing human inositol polyphosphate 5-phosphatase activity.

Gene Expression

In another embodiment, test compounds which increase or decrease inositol polyphosphate 5-phosphatase gene expression are identified. A inositol polyphosphate 5-phosphatase polynucleotide is contacted with a test compound, and the expression of an RNA or polypeptide product of the inositol polyphosphate 5-phosphatase polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of inositol polyphosphate 5-phosphatase mRNA or polypeptide expression in the cells can be determined by methods well known in the art for detecting mRNA or polypeptide. Either qualitative or quantitative methods can be used. The presence of polypeptide products of a inositol polyphosphate 5-phosphatase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a inositol polyphosphate 5-phosphatase polypeptide.

Such screening can be carried out either in a cell-free assay system or in an intact cell. Any cell which expresses a inositol polyphosphate 5-phosphatase polynucleotide can be used in a cell-based assay system. The inositol polyphosphate 5-phosphatase polynucleotide can be naturally occurring in the cell or can be introduced using techniques such as those described above. Either a primary culture or an established cell line, such as CHO or human embryonic kidney 293 cells, can be used.

Inhibitors of human inositol polyphosphate 5-phosphatase also can be designed as described in Safrany et al., *Biochem.* 33, 10763–69, 1994.

Pharmaceutical Compositions

The invention also provides pharmaceutical compositions which can be administered to a patient to achieve a therapeutic effect. Pharmaceutical compositions of the invention can comprise, for example, a inositol polyphosphate 5-phosphatase polypeptide, inositol polyphosphate 5-phosphatase polynucleotide, ribozymes or antisense oligonucleotides, antibodies which specifically bind to a inositol polyphosphate 5-phosphatase polypeptide, or mimetics, activators, or inhibitors of a inositol polyphosphate 5-phosphatase polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of *Remington's Pharmaceutical Sciences* (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Human inositol polyphosphate 5-phosphatase can be regulated to treat COPD, cancer, diabetes, and asthma.

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Activators and/or inhibitors of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Allergy is a complex process in which environmental antigens induce clinically adverse reactions. The inducing antigens, called allergens, typically elicit a specific IgE response and, although in most cases the allergens themselves have little or no intrinsic toxicity, they induce pathology when the IgE response in turn elicits an IgE-dependent or T cell-dependent hypersensitivity reaction. Hypersensitivity reactions can be local or systemic and typically occur within minutes of allergen exposure in individuals who have previously been sensitized to an allergen. The hypersensitivity reaction of allergy develops when the allergen is recognized by IgE antibodies bound to specific receptors on the surface of effector cells, such as mast cells, basophils, or eosinophils, which causes the activation of the effector cells and the release of mediators that produce the acute signs and symptoms of the reactions. Allergic diseases include asthma, allergic rhinitis (hay fever), atopic dermatitis, and anaphylaxis.

Asthma is though to arise as a result of interactions between multiple genetic and environmental factors and is characterized by three major features: 1) intermittent and reversible airway obstruction caused by bronchoconstriction, increased mucus production, and thickening of the walls of the airways that leads to a narrowing of the airways, 2) airway hyperresponsiveness caused by a decreased control of airway caliber, and 3) airway inflammation. Certain cells are critical to the inflammatory reaction of asthma and they include T cells and antigen presenting cells, B cells that produce IgE, and mast cells, basophils, eosinophils, and other cells that bind IgE. These effector cells accumulate at the site of allergic reaction in the airways and release toxic products that contribute to the acute pathology and eventually to the tissue destruction related to the disorder. Other resident cells, such as smooth muscle cells, lung epithelial cells, mucus-producing cells, and nerve cells may also be abnormal in individuals with asthma and may contribute to the pathology. While the airway obstruction of asthma, presenting clinically as an intermittent wheeze and shortness of breath, is generally the most pressing symptom of the disease requiring immediate treatment, the inflammation and tissue destruction associated with the disease can lead to irreversible changes that eventually make asthma a chronic disabling disorder requiring long-term management.

Despite recent important advances in our understanding of the pathophysiology of asthma, the disease appears to be increasing in prevalence and severity (Gergen and Weiss, Am. Rev. Respir. Dis. 146, 823–24, 1992). It is estimated that 30–40% of the population suffer with atopic allergy, and 15% of children and 5% of adults in the population suffer from asthma (Gergen and Weiss, 1992). Thus, an enormous burden is placed on our health care resources. However, both diagnosis and treatment of asthma are difficult. The severity of lung tissue inflammation is not easy to measure and the symptoms of the disease are often indistinguishable from those of respiratory infections, chronic respiratory inflammatory disorders, allergic rhinitis, or other respiratory disorders. Often, the inciting allergen cannot be determined, making removal of the causative environmental agent difficult. Current pharmacological treatments suffer their own set of disadvantages. Commonly used therapeutic agents, such as beta activators, can act as symptom relievers to transiently improve pulmonary function, but do not affect the underlying inflammation. Agents that can reduce the underlying inflammation, such as anti-inflammatory steroids, can have major drawbacks that range from immunosuppression to bone loss (Goodman and Gilman's The Pharmacologic Basis Of Therapeutics, Seventh Edition, MacMillan Publishing Company, NY, USA, 1985). In addition, many of the present therapies, such as inhaled corticosteroids, are short-lasting, inconvenient to use, and must be used often on a regular basis, in some cases for life, making failure of patients to comply with the treatment a major problem and thereby reducing their effectiveness as a treatment.

Because of the problems associated with conventional therapies, alternative treatment strategies have been evaluated. Glycophorin A (Chu and Sharom, Cell. Immunol. 145, 223–39, 1992), cyclosporin (Alexander et al., Lancet 339, 324–28, 1992), and a nonapeptide fragment of IL-2 (Zav'yalov et al., Immunol. Lett. 31, 285–88, 1992) all inhibit interleukin-2 dependent T lymphocyte proliferation; however, they are known to have many other effects. For example, cyclosporin is used as a immunosuppressant after organ transplantation. While these agents may represent alternatives to steroids in the treatment of asthmatics, they inhibit interleukin-2 dependent T lymphocyte proliferation and potentially critical immune functions associated with homeostasis. Other treatments that block the release or activity of mediators of bronchochonstriction, such as cromones or anti-leukotrienes, have recently been introduced for the treatment of mild asthma, but they are expensive and not effective in all patients and it is unclear whether they have any effect on the chronic changes associated with asthmatic inflammation. What is needed in the art is the identification of a treatment that can act in pathways critical to the development of asthma_that both blocks the episodic attacks of the disorder and preferentially dampens the hyperactive allergic immune response without immunocompromising the patient.

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, Pulmonary Diseases and Disorders, 3d ed., New York, McGraw-Hill, 1998, pp. 659–681, 1998; Barnes, Chest 117, 10S-14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type 1 diabetes is initiated by an autoimuune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Human inositol polyphosphate 5-phosphatase is expressed in islets (FIG. 16). It therefore represents a potential target for the treatment of diabetes. Likewise, agents that reduces new blood vessel growth can be used to treat the eye complications that develop in both diseases.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a inositol polyphosphate 5-phosphatase polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects inositol polyphosphate 5-phosphatase activity can be administered to a human cell, either in vitro or in vivo, to reduce inositol polyphosphate 5-phosphatase activity. The reagent preferably binds to an expression product of a human inositol polyphosphate 5-phosphatase gene. If the expression product is a protein, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 $\mu$g of DNA per 16 nmole of liposome delivered to about $10^6$ cells, more preferably about 1.0 $\mu$g of DNA per 16 nmole of liposome delivered to about $10^6$ cells, and even more preferably about 2.0 $\mu$g of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 $\mu$g to about 10 $\mu$g of polynucleotide is combined with about 8 nmol of liposomes, more preferably from about 0.5 $\mu$g to about 5 $\mu$g of polynucleotides are combined with about 8 nmol liposomes, and even more preferably about 1.0 $\mu$g of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202–05 (1993); Chiou et al., Gene Therapeutics: Methods and Applications of Direct Gene Transfer (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases inositol polyphosphate 5-phosphatase activity relative to the inositol polyphosphate 5-phosphatase activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a inositol polyphosphate 5-phosphatase gene or the activity of a inositol polyphosphate 5-phosphatase polypeptide by at least about 10, preferably about 50, more preferably about 75, 90, or 100% relative to the absence of the reagent. The effectiveness of the mechanism chosen to decrease the level of expression of a inositol polyphosphate 5-phosphatase gene or the activity of a inositol polyphosphate 5-phosphatase polypeptide can be assessed using methods well known in the art, such as hybridization of nucleotide probes to inositol polyphosphate 5-phosphatase-specific mRNA, quantitative RT-PCR, immunologic detection of a inositol polyphosphate 5-phosphatase polypeptide, or measurement of inositol polyphosphate 5-phosphatase activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human inositol polyphosphate 5-phosphatase also can be used in diagnostic assays for detecting diseases and abnormalities or susceptibility to diseases and abnormalities related to the presence of mutations in the nucleic acid sequences which encode the enzyme. For example, differences can be determined between the cDNA or genomic sequence encoding inositol polyphosphate 5-phosphatase in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S 1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a inositol polyphosphate 5-phosphatase also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Inositol Polyphosphate 5-phosphatase Activity

The polynucleotide of SEQ ID NO: 1 is inserted into the expression vector pCEV4 and the expression vector pCEV4-inositol polyphosphate 5-phosphatase polypeptide obtained is transfected into human embryonic kidney 293 cells. From these cells extracts are obtained and inositol polyphosphate 5-phosphatase activity is carried out using [3H]Ins(1, 3, 4)P3, [3H]Ins(1, 4, 5)P3, and [3H]Ins(1, 3, 4, 5)P4. The separation of inositol polyphosphates by high performance liquid chromatography is done according to the method of Zhang and Buxton. The flow rate is 0.6 ml/min, and each fraction is collected for 30 s. Collected samples are diluted to 1/20 volume with distilled water and quantitated by liquid scintillation counting. For the assay of Ins(1,3,4)P3 hydrolyzing activity, the D-5 position phosphate of Ins (1, 3, 4, 5)P4 is hydrolyzed by recombinant SHIP 1 protein and used as a substrate. The SHIP 1 protein is prepared the same way as the present inositol polyphosphate 5-phosphatase polypeptide. The PtdIns(4,5)P2 phosphatase activity is determined. The spots on the thin layer chromatography plate are visualized by exposing the plate to x-ray film (Eastman Kodak Scientific Co., Rochester, N.Y.) for 6 days at −80° C. Before the exposure, the intensity of the radioactivity was enhanced by EN3HANCE spray (NEN Life Science Products). It is shown that the polypeptide of SEQ ID NO: 2 has a inositol polyphosphate 5-phosphatase activity.

EXAMPLE 2
Expression of Recombinant Human Inositol Polyphosphate 5-phosphatase The Pichia pastoris expression vector pPICZB (Invitrogen, San Diego, Calif.) is used to produce large quantities of recombinant human inositol polyphosphate 5-phosphatase polypeptides in yeast. The inositol polyphosphate 5-phosphatase-encoding DNA sequence is derived from SEQ ID NOS:1 AND 11. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human inositol polyphosphate 5-phosphatase polypeptide is obtained.

EXAMPLE 3
Identification of Test Compounds that Bind to Inositol Polyphosphate 5-phosphatase Polypeptides Purified inositol polyphosphate 5-phosphatase polypeptides comprising a glutathione-S-transferase protein and absorbed onto glutathione-derivatized wells of 96-well microtiter plates are contacted with test compounds from a small molecule library at pH 7.0 in a physiological buffer solution. Human inositol polyphosphate 5-phosphatase polypeptides comprise the amino acid sequence shown in SEQ ID NOS:2 AND 12. The test compounds comprise a fluorescent tag. The samples are incubated for 5 minutes to one hour. Control samples are incubated in the absence of a test compound.

The buffer solution containing the test compounds is washed from the wells. Binding of a test compound to a inositol polyphosphate 5-phosphatase polypeptide is detected by fluorescence measurements of the contents of the wells. A test compound which increases the fluorescence in a well by at least 15% relative to fluorescence of a well in which a test compound is not incubated is identified as a compound which binds to a inositol polyphosphate 5-phosphatase polypeptide.

EXAMPLE 4
Identification of a Test Compound which Decreases Inositol Polyphosphate 5-phosphatase Gene Expression A test compound is administered to a culture of human cells transfected with a inositol polyphosphate 5-phosphatase expression construct and incubated at 37° C. for 10 to 45 minutes. A culture of the same type of cells which have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled inositol polyphosphate 5-phosphatase-specific probe at 65° C. in Express-hyb (CLONTECH). The probe comprises at least 11 contiguous nucleotides selected from the complement of SEQ ID NOS:1 AND 11. A test compound which decreases the inositol polyphosphate 5-phosphatase-specific signal relative to the signal obtained in the absence of the test compound is identified as an inhibitor of inositol polyphosphate 5-phosphatase gene expression.

EXAMPLE 5
Identification of a Test Compound which Decreases Inositol Polyphosphate 5-phosphatase Activity A test compound is administered to a culture of human cells transfected with a inositol polyphosphate 5-phosphatase expression construct and incubated at 37° C. for 10 to 45 minutes. A culture of the same type of cells which have not been transfected is incubated for the same time without the test compound to provide a negative control. Enzyme activity is measured using the method described in U.S. Pat. No. 6,090,621. Inositol polyphosphate 5-phosphatases hydrolyze the 5 phosphate from Ins(1,4,5)P$_3$ and Ins(1,3,4,5)P$_4$; a subset of these enzymes can remove the 5-phosphate from phosphatidylinositol polyphosphates. To determine whether the enzyme of the invention is a functional inositol phosphatase in the presence of various test compounds, anti-human inositol polyphosphate 5-phosphatase immunoprecipitates are assayed for their ability to hydrolyze inositol phosphates and phosphatidylinositol polyphosphates.

A test compound which decreases the enzyme activity of the inositol polyphosphate 5-phosphatase relative to the enzyme activity in the absence of the test compound is identified as an inhibitor of inositol polyphosphate 5-phosphatase activity.

EXAMPLE 6
Tissue-specific Expression of Human Inositol Polyphosphate 5-phosphatase The qualitative expression pattern of inositol polyphosphate 5-phosphatase in various tissues is determined by Reverse Transcription-Polymerase Chain Reaction (RT-PCR). To demonstrate that inositol polyphosphate 5-phosphatase is involved in the disease process of asthma, the following whole body panel is screened to show predominant or relatively high expression in lung or immune tissues: brain, heart, kidney, liver, lung, trachea, bone marrow, colon, small intestine, spleen, stomach, thymus, mammary gland, skeletal muscle, prostate, testis, uterus, cerebellum, fetal brain, fetal liver, spinal cord, placenta, adrenal gland, pancreas, salivary gland, thyroid, peripheral blood leukocytes, lymph node, and tonsil. Once this is established, the following lung and immune system cells are screened to localize expression to particular cell subsets: lung microvascular endothelial cells, bronchial/tracheal epithelial cells, bronchial/tracheal smooth muscle cells, lung fibroblasts, T cells (T helper 1 subset, T helper 2 subset, NKT cell subset, and cytotoxic T lymphocytes), B cells, mononuclear cells (monocytes and macrophages), mast cells, eosinophils, neutrophils, and dendritic cells. As a final step, the expression of inositol polyphosphate 5-phosphatase in cells derived from normal individuals with the expression of cells derived from asthmatic individuals is compared.

To demonstrate that inositol polyphosphate 5-phosphatase is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI-H460 (lung), HT-116 (colon), DLD-1 (colon), MDA-MD-231 (breast), LS174T (colon), ZF-75 (breast), MDA-MN-435 (breast), HT-1080, MCF-7 (breast), and U87. Matched pairs of malignant and normal tissue from the same patient also are tested.

To demonstrate that inositol polyphosphate 5-phosphatase is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus. As a final step, the expression of human inositol polyphosphate 5-phosphatase in cells derived from normal individuals with the expression of cells derived from COPD-affected individuals is compared.

To demonstrate that human inositol polyphosphate 5-phosphatase is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of human inositol polyphosphate 5-phosphatase in cells derived from normal individuals with the expression of cells derived from diabetic individuals is compared. Quantitative expression profiling. Quantitative expression profiling is performed by the form of quantitative PCR analysis called "kinetic analysis" firstly described in Higuchi et al., *BioTechnology* 10, 413–17, 1992, and Higuchi et al., *BioTechnology* 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'-3' endonuclease activity of Taq DNA polymerase and a fluorescent dye released in the medium (Holland et al., *Proc. Natl. Acad. Sci. U.S.A.* 88, 7276–80, 1991). Because the fluorescence emission will increase in direct proportion to the amount of the specific amplified product, the exponential growth phase of PCR product can be detected and used to determine the initial template concentration (Heid et al., *Genome Res.* 6, 986–94, 1996, and Gibson et al., *Genome Res.* 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty $\mu$g of each RNA were treated with DNase I for 1 hour at 37° C. in the following reaction mix: 0.2 U/$\mu$l RNase-free DNase I (Roche Diagnostics, Germany); 0.4 U/$\mu$l RNase inhibitor (PE Applied Biosystems, Calif.); 10 mM Tris-HCl pH 7.9; 10 mM $MgCl_2$; 50 mM NaCl; and 1 mM DTT.

After incubation, RNA is extracted once with 1 volume of phenol:chloroform:isoamyl alcohol (24:24:1) and once with chloroform, and precipitated with 1/10 volume of 3 M NaAcetate, pH 5.2, and 2 volumes of ethanol.

Fifty $\mu$g of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, Calif.) according to the manufacturer's protocol. The final concentration of RNA in the reaction mix is 200 ng/$\mu$L. Reverse transcription is carried out with 2.5 $\mu$M of random hexamer primers.

TaqMan quantitative analysis. Specific primers and probe are designed according to the recommendations of PE Applied Biosystems. Probes can be labeled at the 5' end with FAM (6-carboxyfluorescein) and at the 3' end with TAMRA (6-carboxyttramethylrhodamine. Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, Calif.).

The assay reaction mix is as follows: 1×final TaqMan Universal PCR Master Mix (from 2× stock) (PE Applied Biosystems, CA); 1×PDAR control—18S RNA (from 20× stock); 300 nM forward primer; 900 nM reverse primer; 200 nM probe; 10 ng cDNA; and water to 25 ml.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7
Diabetes: In Vivo Testing of Compounds/Target Validation

1. Glucose Production

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

2. Insulin Sensitivity

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

3. Insulin Secretion

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

Compounds that enhance insulin secretion from the pancreas will increase plasma insulin levels and improve the disappearance of plasma glucose following the administration of a glucose load. When measuring insulin levels, test compounds which regulate pristanoyl-CoA oxidase-like enzyme are administered by different routes (p.o., i.p., s.c., or i.v.) to overnight fasted normal rats or mice. At the appropriate time an intravenous glucose load (0.4 g/kg) is given, blood is collected one minute later. Plasma insulin levels are determined. Test compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60, and 90 minutes and plasma glucose levels determined. Test compounds that increase insulin levels will decrease glucose levels and the area-under-the glucose curve when compared to the vehicle-treated group given only glucose.

4. Glucose Production

Over-production of glucose by the liver, due to an enhanced rate of gluconeogenesis, is the major cause of fasting hyperglycemia in diabetes. Overnight fasted normal rats or mice have elevated rates of gluconeogenesis as do streptozotocin-induced diabetic rats or mice fed ad libitum. Rats are made diabetic with a single intravenous injection of 40 mg/kg of streptozotocin while C57BL/KsJ mice are given 40–60 mg/kg i.p. for 5 consecutive days. Blood glucose is measured from tail-tip blood and then compounds are administered via different routes (p.o., i.p., i.v., s.c.). Blood is collected at various times thereafter and glucose measured. Alternatively, compounds are administered for several days, then the animals are fasted overnight, blood is collected and plasma glucose measured. Compounds that inhibit glucose production will decrease plasma glucose levels compared to the vehicle-treated control group.

5. Insulin Sensitivity

Both ob/ob and db/db mice as well as diabetic Zucker rats are hyperglycemic, hyperinsulinemic and insulin resistant. The animals are pre-bled, their glucose levels measured, and then they are grouped so that the mean glucose level is the same for each group. Compounds are administered daily either q.d. or b.i.d. by different routes (p.o., i.p., s.c.) for 7–28 days. Blood is collected at various times and plasma glucose and insulin levels determined. Compounds that improve insulin sensitivity in these models will decrease both plasma glucose and insulin levels when compared to the vehicle-treated control group.

6. Insulin Secretion

Compounds that enhance insulin secretion from the pancreas will increase plasma insulin levels and improve the disappearance of plasma glucose following the administration of a glucose load. When measuring insulin levels, compounds are administered by different routes (p.o., i.p., s.c. or i.v.) to overnight fasted normal rats or mice. At the appropriate time an intravenous glucose load (0.4 g/kg) is given, blood is collected one minute later. Plasma insulin levels are determined. Compounds that enhance insulin secretion will increase plasma insulin levels compared to animals given only glucose. When measuring glucose disappearance, animals are bled at the appropriate time after compound administration, then given either an oral or intraperitoneal glucose load (1 g/kg), bled again after 15, 30, 60 and 90 minutes and plasma glucose levels determined. Compounds that increase insulin levels will decrease glucose levels and the area-under-the glucose curve when compared to the vehicle-treated group given only glucose.

EXAMPLE 8
Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NOS:1 AND 11 is used as the test oligonucleotide. As a control, another (random) sequence is used: 5'-TCA ACT GAC TAG ATG TAC ATG GAC-3'. Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 μM once per day for seven days.

The addition of the test oligonucleotide for seven days results in significantly reduced expression of human inositol polyphosphate 5-phosphatase as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human inositol polyphosphate 5-phosphatase has an anti-proliferative effect on cancer cells.

EXAMPLE 9

In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value $\leq 0.05$ compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p \leq 0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3. Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models 3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a pre-determined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary (Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

What is claimed is:

1. An isolated and purified protein comprising the amino acid sequence shown in SEQ ID NO:12.

2. The protein of claim 1 further comprising an additional polypeptide comprising an amino acid sequence which is not the amino acid sequence shown in SEQ ID NO:12, wherein the additional polypeptide is joined to the protein by means of a peptide bond.

3. A method of screening for candidate therapeutic agents, comprising the steps of:

contacting a protein comprising the amino acid sequence shown in SEQ ID NO:12 with a test compound;

assaying for binding between the protein and the test compound; and identifying a test compound that binds to the protein as a candidate therapeutic agent that may be useful for treating a disorder selected from the group consisting of chronic obstructive pulmonary disease, asthma, diabetes, and cancer.

4. The method of claim 3 wherein either the test compound or the protein comprises a detectable label.

5. The method of claim 3 wherein either the test compound or the protein is bound to a solid support.

* * * * *

SEQUENCE LISTING

```
<160> NUMBER OF SEQ ID NOS: 12

<210> SEQ ID NO 1
<211> LENGTH: 2256
<212> TYPE: DNA
<213> ORGANISM: Homo sapiens

<400> SEQUENCE: 1
atgccaaaag agaggcaaac accaggttct tataatgtcg tcgtctggtt tctaactgtg      60
gtgatgaagc atagttacac tggtgaagtt gaagtcattg atgatcacag agctaggaaa     120
actgctgtga acctcacagg cagggaagcc ctcccagata accccttctt tcacattccc     180
acaatatcct gtatcaccct ctacaccttt gcagatggta gccatagcat gacctccctc     240
atggcgggcc tgggtcaggg tgaccaggga gagaaaggaa ggaggacaga ccctcggtac     300
cgttgccatc ctcaggctgg gaagtgggag cctgtgcctt taaattctca gcaggttgaa     360
atggctgatg acatcactgg ttcccgggag cggatcactg tggtcacatg gaacgtgggc     420
actgccatgc ccccagacga tgtcacatcc ctcctccacc tgggcggtgg tgacgacagc     480
gacggcgcag acatgatcgc cataggggttg caggaagtga actccatgct caacaagcga     540
ctcaaggacg ccctcttcac ggaccagtgg agtgagctgt tcatggatgc gctagggccc     600
ttcaacttcg tgctggtaac gcaccccctca cccccctggac agccagagac cctgctgaat     660
tcctggctcc agctgtaccc tggctcactg tggggcccgc tgggcctctg tggctgggtg     720
agttcggtga ggatgcaggg tgtcatcctg ctgctgttcg ccaagtacta ccacctgccc     780
ttcctgcgag acgtgcagac cgactgcacg cgcactggcc tgggcggcta ctggggtaac     840
aagggtggcg tgagcgtgcg cctggcggcc ttcgggcaca tgctctgctt cctgaactgc     900
cacttgcctg cgcatatgga caaggcggag cagcgcaaag acaacttcca gaccatcctc     960
agcctccagc agttccaagg gccgggcgca cagggcatcc tggatcatga gtatgggctg    1020
ggcctcgtgt tctggttcgg ggacctgaac ttccgcattg agagctatga cctgcacttt    1080 gtcaagttt g ccatcgacag tgaccagctc catcagctct gggagaagga ccagctcaac    1140
```

```
atggccaaga cacctggcc cattctgaag ggctttcagg aggggcccct caacttcgct    1200
cccaccttca gtttgatgt gggtaccaac aaatacgata ccagtgccaa gaaacggaag    1260
ccagcttgga cagaccgtat cctatggaag gtcaaggctc caggtggggg tcccagcccc    1320
tcaggacgga agagccaccg actccaggtg acgcagcaca gctaccgcag ccacatggaa    1380
tacacagtca gcgaccacaa gcctgtggct gcccagttcc tcctgcagtt tgccttcagg    1440
gacgacatgc cactggtgcg gctggaggtg gcagatgagt gggtgcggcc cgagcaggcg    1500
gtggtgaggt accgcatgga aacagtgttc gcccgcagct cctgggactg gatcggctta    1560
taccgggtgg gtttccgcca ttgcaaggac tatgtggctt atgtctgggc caaacatgaa    1620
gatgtggatg gaataccta ccaggtaaca ttcagtgagg aatcactgcc caagggccat    1680
ggagacttca tcctgggcta ctatagtcac aaccacagca tcctcatcgg catcactgaa    1740
cccttccaga tctcgctgcc ttcctcggag ttggccagca gcagcacaga cagctcaggc    1800
accagctcag agggagagga tgacagcaca ctggagctcc ttgcacccaa gtcccgcagc    1860
cccagtcctg gcaagtccaa gcgacaccgc agccgcagcc cgggactggc caggttccct    1920
gggcttgccc tacggccctc atcccgtgaa cgccgtggtg ccagccgtag ccctcaccc     1980 cagagccgcc gcctgtcccg agtggctcct gacaggagca gtaatggcag cagccggggc    2040
agtagtgaag aggggccctc tgggttgcct ggcccctggg ccttccacc agctgtgcct    2100 cgaagcctgg gcctgttgcc cgccttgcgc ctagagactg tagaccctgg tggtggtggc    2160
tcctggggac ctgatcggga ggccctggcg cccaacagcc tgtctcctag tccccagggc    2220
catcgggggc tggaggaagg gggcctgggg ccctga                              2256
```

<210> SEQ ID NO 2
<211> LENGTH: 751
<212> TYPE: PRT
<213> ORGANISM: Homo sapiens

<400> SEQUENCE: 2

```
Met Pro Lys Glu Arg Gln Thr Pro Gly Ser Tyr Asn Val Val Trp
1               5                   10                  15

Phe Leu Thr Val Val Met Lys His Ser Tyr Thr Gly Glu Val Glu Val
                20                  25                  30

Ile Asp Asp His Arg Ala Arg Lys Thr Ala Val Asn Leu Thr Gly Arg
            35                  40                  45

Glu Ala Leu Pro Asp Asn Pro Phe Phe His Ile Pro Thr Ile Ser Cys
        50                  55                  60

Ile Thr Leu Tyr Thr Phe Ala Asp Gly Ser His Ser Met Thr Ser Leu
65                  70                  75                  80

Met Ala Gly Leu Gly Gln Gly Asp Gln Gly Glu Lys Gly Arg Arg Thr
                85                  90                  95

Asp Pro Arg Tyr Arg Cys His Pro Gln Ala Gly Lys Trp Glu Pro Val
            100                 105                 110

Pro Leu Asn Ser Gln Gln Val Glu Met Ala Asp Asp Ile Thr Gly Ser
        115                 120                 125

Arg Glu Arg Ile Thr Val Val Thr Trp Asn Val Gly Thr Ala Met Pro
    130                 135                 140

Pro Asp Asp Val Thr Ser Leu Leu His Leu Gly Gly Asp Asp Ser
145                 150                 155                 160

Asp Gly Ala Asp Met Ile Ala Ile Gly Leu Gln Glu Val Asn Ser Met
                165                 170                 175
```

```
Leu Asn Lys Arg Leu Lys Asp Ala Leu Phe Thr Asp Gln Trp Ser Glu
            180                 185                 190
Leu Phe Met Asp Ala Leu Gly Pro Phe Asn Phe Val Leu Val Thr His
        195                 200                 205
Pro Ser Pro Pro Gly Gln Pro Glu Thr Leu Leu Asn Ser Trp Leu Gln
        210                 215                 220
Leu Tyr Pro Gly Ser Leu Trp Gly Pro Leu Gly Leu Cys Gly Trp Val
225                 230                 235                 240
Ser Ser Val Arg Met Gln Gly Val Ile Leu Leu Phe Ala Lys Tyr
                245                 250                 255
Tyr His Leu Pro Phe Leu Arg Asp Val Gln Thr Asp Cys Thr Arg Thr
                260                 265                 270
Gly Leu Gly Gly Tyr Trp Gly Asn Lys Gly Val Ser Val Arg Leu
                275                 280                 285
Ala Ala Phe Gly His Met Leu Cys Phe Leu Asn Cys His Leu Pro Ala
        290                 295                 300
His Met Asp Lys Ala Glu Gln Arg Lys Asp Asn Phe Gln Thr Ile Leu
305                 310                 315                 320
Ser Leu Gln Gln Phe Gln Gly Pro Gly Ala Gln Gly Ile Leu Asp His
                325                 330                 335
Glu Tyr Gly Leu Gly Leu Val Phe Trp Phe Gly Asp Leu Asn Phe Arg
            340                 345                 350
Ile Glu Ser Tyr Asp Leu His Phe Val Lys Phe Ala Ile Asp Ser Asp
            355                 360                 365
Gln Leu His Gln Leu Trp Glu Lys Asp Gln Leu Asn Met Ala Lys Asn
        370                 375                 380
Thr Trp Pro Ile Leu Lys Gly Phe Gln Glu Gly Pro Leu Asn Phe Ala
385                 390                 395                 400
Pro Thr Phe Lys Phe Asp Val Gly Thr Asn Lys Tyr Asp Thr Ser Ala
                405                 410                 415
Lys Lys Arg Lys Pro Ala Trp Thr Asp Arg Ile Leu Trp Lys Val Lys
                420                 425                 430
Ala Pro Gly Gly Gly Pro Ser Pro Ser Gly Arg Lys Ser His Arg Leu
            435                 440                 445
Gln Val Thr Gln His Ser Tyr Arg Ser His Met Glu Tyr Thr Val Ser
        450                 455                 460
Asp His Lys Pro Val Ala Ala Gln Phe Leu Leu Gln Phe Ala Phe Arg
465                 470                 475                 480
Asp Asp Met Pro Leu Val Arg Leu Glu Val Ala Asp Glu Trp Val Arg
                485                 490                 495
Pro Glu Gln Ala Val Val Arg Tyr Arg Met Glu Thr Val Phe Ala Arg
            500                 505                 510
Ser Ser Trp Asp Trp Ile Gly Leu Tyr Arg Val Gly Phe Arg His Cys
        515                 520                 525
Lys Asp Tyr Val Ala Tyr Val Trp Ala Lys His Glu Asp Val Asp Gly
530                 535                 540
Asn Thr Tyr Gln Val Thr Phe Ser Glu Glu Ser Leu Pro Lys Gly His
545                 550                 555                 560
Gly Asp Phe Ile Leu Gly Tyr Tyr Ser His Asn His Ser Ile Leu Ile
                565                 570                 575
Gly Ile Thr Glu Pro Phe Gln Ile Ser Leu Pro Ser Ser Glu Leu Ala
                580                 585                 590
```

```
Ser Ser Ser Thr Asp Ser Ser Gly Thr Ser Ser Glu Gly Glu Asp Asp
        595                 600                 605

Ser Thr Leu Glu Leu Leu Ala Pro Lys Ser Arg Ser Pro Ser Pro Gly
        610                 615                 620

Lys Ser Lys Arg His Arg Ser Arg Ser Pro Gly Leu Ala Arg Phe Pro
625                 630                 635                 640

Gly Leu Ala Leu Arg Pro Ser Arg Glu Arg Arg Gly Ala Ser Arg
                645                 650                 655

Ser Pro Ser Pro Gln Ser Arg Arg Leu Ser Arg Val Ala Pro Asp Arg
                660                 665                 670

Ser Ser Asn Gly Ser Ser Arg Gly Ser Ser Glu Glu Gly Pro Ser Gly
        675                 680                 685

Leu Pro Gly Pro Trp Ala Phe Pro Pro Ala Val Pro Arg Ser Leu Gly
        690                 695                 700

Leu Leu Pro Ala Leu Arg Leu Glu Thr Val Asp Pro Gly Gly Gly
705                 710                 715                 720

Ser Trp Gly Pro Asp Arg Glu Ala Leu Ala Pro Asn Ser Leu Ser Pro
                725                 730                 735

Ser Pro Gln Gly His Arg Gly Leu Glu Glu Gly Leu Gly Pro
        740                 745                 750

<210> SEQ ID NO 3
<211> LENGTH: 1001
<212> TYPE: PRT
<213> ORGANISM: Rattus norvegicus

<400> SEQUENCE: 3

Met Glu Gly Gln Ser Arg Ser Gly Ser Ala Lys Ser Gly Thr Arg Thr
1               5                   10                  15

Gly Leu Gly Pro Leu Pro Gly Thr His Gly Ala Leu Gln Thr Gly Thr
            20                  25                  30

Pro Ser Lys Lys Val Asn Ser Ser Phe Gln Leu Pro Ala Lys Asn Thr
        35                  40                  45

Gly Pro Thr Pro Ser Glu Pro Arg Leu Ala Leu Ala Pro Val Gly Pro
    50                  55                  60

Arg Ala Ala Val Ser Pro Pro Ser Glu Arg Pro Arg Leu Ala Leu Ser
65                  70                  75                  80

Ser Pro Arg Pro Ile Leu Ala Pro Leu Ser Thr Ala Gly Glu Gln Lys
                85                  90                  95

Arg Pro Pro Pro His Arg Ser Ser Lys Pro Ala Pro Thr Ser Val Gly
            100                 105                 110

Gln Leu Val Val Ser Ala Ala Ala Gly Pro Lys Pro Pro Pro Val Ala
        115                 120                 125

Ser Val Ser Ile Leu Ala Pro Lys Ser Leu Gly Gln Leu Val Ile Ser
    130                 135                 140

Ala Ser Ala Met Pro Arg Pro Thr Pro Ala Pro Leu Gly Pro Ile Leu
145                 150                 155                 160

Ser Pro Thr Ser Arg Asp Gln Lys Gln Leu Ser Pro Thr Ser Val Gly
                165                 170                 175

Pro Lys Pro Ala Leu Ala Thr Ser Gly Leu Ser Leu Ala Leu Ala Ser
            180                 185                 190

Gln Glu Gln Pro Pro Gln Ser Pro Ser Ser Pro Val Pro Ser
        195                 200                 205

Pro Val Leu Ser Pro Ser Gln Glu Ser His Leu Ala Pro Ala Thr Val
    210                 215                 220
```

```
Thr Ser Thr Pro Ala Ser Glu Arg Gln Leu Pro Ala Arg Gln Lys Asp
225                 230                 235                 240

Thr Ala Val Arg Arg Pro Ile Pro Pro Ala Asp Gly Cys Leu His Thr
            245                 250                 255

Pro Val Gln Ala Ala Gly Leu Ala Thr Ser Pro Pro Arg Ala Gln Thr
        260                 265                 270

Ser Ser Asp Pro Arg Leu Ser Pro Ser Phe Arg Ala Arg Pro Glu Ala
    275                 280                 285

Pro Arg His Ser Pro Glu Asp Pro Val Leu Pro Pro Pro Pro Gln Thr
290                 295                 300

Leu Pro Leu Asp Val Ser Ser Gly Leu Pro Glu Ser Gly Thr Arg Ser
305                 310                 315                 320

Pro Gly Leu Leu Ser Pro Thr Phe Arg Pro Gly Ile Pro Ser Asn Gln
            325                 330                 335

Thr Val Pro Pro Pro Leu Pro Lys Pro Pro Arg Ser Pro Ser Arg Ser
        340                 345                 350

Pro Ser Arg Ser Pro Asn Arg Ser Pro Cys Val Pro Ala Pro Glu
    355                 360                 365

Val Ala Leu Pro Arg Pro Val Thr Gln Gly Ala Gly Pro Gly Lys Cys
370                 375                 380

Pro Ser Pro Asn Leu Gln Thr Gln Glu Ser Pro Val Ala Thr Ala Thr
385                 390                 395                 400

Ser Pro Thr Ser Ser Trp Ser Ala Gln Pro Thr Cys Lys Ser Asp Pro
            405                 410                 415

Gly Phe Arg Ile Thr Val Val Thr Trp Asn Val Gly Thr Ala Met Pro
        420                 425                 430

Pro Asp Asp Val Thr Ser Leu Leu His Leu Gly Gly His Asp Ser
    435                 440                 445

Asp Gly Ala Asp Met Ile Ala Ile Gly Leu Gln Glu Val Asn Ser Met
450                 455                 460

Ile Asn Lys Arg Leu Lys Asp Ala Leu Phe Thr Asp Gln Trp Ser Glu
465                 470                 475                 480

Leu Phe Met Asp Ala Leu Gly Pro Phe Asn Phe Val Leu Val Ser Thr
            485                 490                 495

Val Arg Met Gln Gly Val Ile Leu Leu Leu Phe Ala Lys Tyr Tyr His
        500                 505                 510

Leu Pro Phe Leu Arg Asp Val Gln Thr Asp Cys Thr Arg Thr Gly Leu
    515                 520                 525

Gly Gly Tyr Trp Gly Asn Lys Gly Gly Val Ser Val Arg Leu Ala Ala
530                 535                 540

Phe Gly His Met Leu Cys Phe Leu Asn Cys His Leu Pro Ala His Met
545                 550                 555                 560

Asp Lys Ala Glu Gln Arg Lys Asp Asn Phe Gln Thr Ile Leu Ser Leu
            565                 570                 575

Gln Gln Phe Gln Gly Pro Gly Ala His Gly Ile Leu Asp His Asp Leu
        580                 585                 590

Val Phe Trp Phe Gly Asp Leu Asn Phe Arg Ile Glu Ser Tyr Asp Leu
    595                 600                 605

His Phe Val Lys Phe Ala Ile Asp Ser Asn Gln Leu His Gln Leu Trp
610                 615                 620

Glu Lys Asp Gln Leu Asn Met Ala Lys Asn Thr Trp Pro Ile Leu Lys
625                 630                 635                 640
```

-continued

```
Gly Phe Gln Glu Gly Pro Leu Asn Phe Ala Pro Thr Phe Lys Phe Asp
                645                 650                 655
Val Gly Thr Asn Lys Tyr Asp Thr Ser Ala Lys Lys Arg Lys Pro Ala
            660                 665                 670
Trp Thr Asp Arg Ile Leu Trp Lys Val Lys Ala Pro Ser Gly Gly Pro
        675                 680                 685
Ser Pro Ser Gly Arg Glu Ser His Arg Leu Gln Val Thr Gln His Ser
    690                 695                 700
Tyr Arg Ser His Met Glu Tyr Thr Val Ser Asp His Lys Pro Val Ala
705                 710                 715                 720
Ala Arg Phe Leu Leu Gln Phe Ala Phe Arg Asp Asp Val Pro Leu Val
                725                 730                 735
Arg Leu Glu Val Ala Asp Glu Trp Ala Arg Pro Glu Gln Ala Val Val
            740                 745                 750
Arg Tyr Arg Val Glu Thr Val Phe Ala Arg Ser Ser Trp Asp Trp Ile
        755                 760                 765
Gly Leu Tyr Arg Val Gly Phe Arg His Cys Lys Asp Tyr Val Ala Tyr
    770                 775                 780
Val Trp Ala Lys His Glu Glu Val Asp Gly Asn Ile Tyr Gln Val Thr
785                 790                 795                 800
Phe Ser Glu Glu Ser Leu Pro Lys Gly His Gly Asp Phe Ile Leu Gly
                805                 810                 815
Tyr Tyr Ser His His His Ser Ile Leu Ile Gly Val Thr Glu Pro Phe
            820                 825                 830
Gln Ile Ser Leu Pro Thr Ser Glu Ser Ala Ser Ser Ser Thr Asp Ser
        835                 840                 845
Ser Gly Thr Ser Ser Glu Gly Glu Asp Asp Ser Thr Leu Glu Leu Leu
    850                 855                 860
Ala Pro Lys Ser Arg Ser Pro Ser Pro Gly Lys Ser Lys Arg His Arg
865                 870                 875                 880
Ser Arg Ser Pro Gly Leu Ala Arg Phe Pro Ser Leu Ala Leu Arg Pro
                885                 890                 895
Ser Ser Arg Glu Arg Arg Gly Gly Ser Arg Ser Pro Ser Pro Gln Ser
            900                 905                 910
Arg Gln Leu Pro Arg Val Ala Pro Asp Arg Gly His Ser Ser Gly Ser
        915                 920                 925
Arg Gly Ser Ser Glu Glu Gly Pro Ser Gly Pro Pro Gly Pro Trp Ala
    930                 935                 940
Phe Pro Pro Ala Val Pro Arg Ser Leu Gly Leu Leu Pro Ala Leu Arg
945                 950                 955                 960
Leu Glu Thr Val Asp Pro Gly Gly Gly Ser Trp Gly Pro Asp Gln
                965                 970                 975
Glu Ala Pro Asp Pro Asn Ser Leu Ser Pro Ser Pro Gln Gly Arg Leu
            980                 985                 990
Gly Leu Glu Asp Gly Gly Leu Gly  Pro
        995                 1000
```

<210> SEQ ID NO 4
<211> LENGTH: 464
<212> TYPE: DNA
<213> ORGANISM: Homo sapiens

<400> SEQUENCE: 4
gcgatgagtg cgtgcggccg agccaggcgg tggtgaggta ccgcatggaa acagtgttcg     60

```
cccgcagctc ctgggactgg atcggcttat accgggtggg tttccgccat tgcaaggact      120
atgtggctta tgtctgggcc aaacatgaag atgtggatgg aatacctac caggtaacat       180 tcagtgagga atcactgccc aagggccatg gagacttcat cctgggctac tatagtcaca      240
accacagcat cctcatcggc atcactgaac ccttccagat ctcgctgcct tcctcggagt      300
tggccagcag cagcacagac agctcaggca ccagctcaga gggagaggat gacagcacac      360
tggagctcct tgcacccaag tcccgcagcc ccagtcctgg caagcccaag cgacaccgca      420
gccgcaggcc gggactggcc aggttcactg gcttgccct acgg                        464
```

<210> SEQ ID NO 5
<211> LENGTH: 465
<212> TYPE: DNA
<213> ORGANISM: Homo sapiens

<400> SEQUENCE: 5

```
aagcggatga ggggtgcggc cgagtaggcg gtggtgaggt accgcatgga aacagtgttc      60
gcccgcagct cctgggactg gatcggctta taccgggtgg gtttccgcca ttgcaaggac     120
tatgtggctt atgtctgggc caaacatgaa gatgtggatg gaataccta ccaggtaaca     180 ttcagtgagg aatcactgcc caagggccat ggagacttca tcctgggcta ctatagtcac     240
aaccacagca tcctcatcgg catcactgaa cccttccaga tctcgctgcc ctcctcggag     300
ttggccagca gcagcacaga cagctcaggc accagctcag agggagagga tgacagcaca     360
ctggagctcc ttgcacccaa gtcccgcagc cccagtcctg gcaagtccaa gcgacaccgc     420
agccgcagcc cgggactggc caggttccct gggcttgccc tacgg                     465
```

<210> SEQ ID NO 6
<211> LENGTH: 470
<212> TYPE: DNA
<213> ORGANISM: Homo sapiens
<220> FEATURE:
<221> NAME/KEY: misc_feature
<222> LOCATION: (105)..(105)
<223> OTHER INFORMATION: n=a, c, g or t

<400> SEQUENCE: 6

```
ttggataaag cggatagggg tgcggccgag taggcggtgg tgaggtacgc atggaaacag      60
tgttcgcccg cagctcctgg gactggatcg gcttataccg ggtgngtttc cgccattgca     120
aggactatgt ggcttatgtc tgggccaaac atgaagatgt ggatgggaat acctaccagg     180
taacattcag tgaggaatca ctgcccaagg gccatggaga cttcatcctg gctactata     240 gtcacaacca gcatcctc atcggcatca ctgaacccttt ccagatctcg ctgcctcct      300 cggagttggc cagcagcagc acagacagct caggcaccag ctcagaggga ggatgaca      360 gcacactgga gctccttgca cccaagtccc gcagcccag tcctggcaag tccaagcgac     420
accgcagccg cagcccggga ctggccaggt tccctgggct gccctacgg                470
```

<210> SEQ ID NO 7
<211> LENGTH: 485
<212> TYPE: DNA
<213> ORGANISM: Homo sapiens
<220> FEATURE:
<221> NAME/KEY: misc_feature
<222> LOCATION: (235)..(235)
<223> OTHER INFORMATION: n=a, c, g or t
<220> FEATURE:
<221> NAME/KEY: misc_feature
<222> LOCATION: (340)..(340)
<223> OTHER INFORMATION: n=a, c, g or t

```
<220> FEATURE:
<221> NAME/KEY: misc_feature
<222> LOCATION: (390)..(390)
<223> OTHER INFORMATION: n=a, c, g or t
<220> FEATURE:
<221> NAME/KEY: misc_feature
<222> LOCATION: (469)..(469)
<223> OTHER INFORMATION: n=a, c, g or t

<400> SEQUENCE: 7
ctgcactttg tcaagtttgc catcgacagt gaccagctcc atcagctctg ggagaaggac      60
cagctcaaca tggccaagaa cacctggccc attctgaagg ctttcaggga ggggcccctc     120
aacttcgctc ccaccttcaa gtttgatgtg ggtaccaaca aatacgatac cagtgccaag     180
aaacggaagc cagcttggac agaccgtatc ctatggaagg tcaaggctcc aggtnggggt     240
cccagcccct caggacggaa gagccaccga ctccaggtga cgcagcacag ctaccgcagc     300
cacatggaat acacagtcag cgaccacaag cctgtggtgn cccagttcct cctggcagtt     360
tgcctttcag ggacgacatg ccactggtgn cggctggagg ttggcagatt gagtgggttg     420
cggcccgagc aggcggtggt gaggttaccg cttgggaaac attttcgnc cgcagttcct     480 gggga                                                                485

<210> SEQ ID NO 8
<211> LENGTH: 468
<212> TYPE: DNA
<213> ORGANISM: Homo sapiens
<220> FEATURE:
<221> NAME/KEY: misc_feature
<222> LOCATION: (3)..(3)
<223> OTHER INFORMATION: n=a, c, g or t
<220> FEATURE:
<221> NAME/KEY: misc_feature
<222> LOCATION: (38)..(38)
<223> OTHER INFORMATION: n=a, c, g or t
<220> FEATURE:
<221> NAME/KEY: misc_feature
<222> LOCATION: (407)..(407)
<223> OTHER INFORMATION: n=a, c, g or t
<220> FEATURE:
<221> NAME/KEY: misc_feature
<222> LOCATION: (431)..(431)
<223> OTHER INFORMATION: n=a, c, g or t

<400> SEQUENCE: 8
aantttgcca tcgacagtga ccagctccat cagctctngg agaaggacca gctcaacatg      60
gccaagaaca cctggcccat tctgaagggc tttcaggagg ggcccctcaa cttcgctccc     120
accttcaagt tgatgtggg taccaacaaa tacgatacca gtgccaagaa acggaagcca     180
gcttggacag accgtatcct atggaaggtc aaggctccag gtggggtcc cagcccctca     240 ggacggaaga gccaccgact ccaggtgacg cagcacagct accgcagcca catggaatac     300
acagtcagcg accacaagcc tgtggttgac ccagttcctc ctgcagtttt gcctttcagg     360
ggacggacat gccactggtg agcggctggg aggtgggcag atgagtnggg tgcgggcccg     420
agcaggcggt nggtgaggtt accgcttggg aaacattttt tcggccgt                 468

<210> SEQ ID NO 9
<211> LENGTH: 711
<212> TYPE: DNA
<213> ORGANISM: Homo sapiens
<220> FEATURE:
<221> NAME/KEY: misc_feature
<222> LOCATION: (529)..(529)
<223> OTHER INFORMATION: n=a, c, g or t
<220> FEATURE:
```

<221> NAME/KEY: misc_feature
<222> LOCATION: (592)..(592)
<223> OTHER INFORMATION: n=a, c, g or t
<220> FEATURE:
<221> NAME/KEY: misc_feature
<222> LOCATION: (672)..(672)
<223> OTHER INFORMATION: n=a, c, g or t
<220> FEATURE:
<221> NAME/KEY: misc_feature
<222> LOCATION: (678)..(678)
<223> OTHER INFORMATION: n=a, c, g or t
<220> FEATURE:
<221> NAME/KEY: misc_feature
<222> LOCATION: (680)..(680)
<223> OTHER INFORMATION: n=a, c, g or t

<400> SEQUENCE: 9

```
gaggctggag aatttaattc ctaatggatg acctccagga gggggacatt tgccagagct    60
ctcccatcat cccagatggg ggcctgggtg gggctttgct gattgtcaca gttgaggtgc   120
caggactgag ttttggggga ccccagttgt ccaccctgg ccaggacaga gaggcaggtg   180
cagatacagc tggaggagca gcaggagaga ggcaggtggg cttgcaaaag attgaggcag   240
aatggtggtc acctttggcc catctgccta ccccaccctc agggcccag gccccttcc    300
tccagccccc gatggccctg ggactaggga gcaggctgt tgggcgccag ggcctcccga   360
tcaggtcccc aggagccacc accaccaggg tctacagtct ctaggcgcaa ggcgggcaac   420
aggcccaggc ttcgaggcac agctggtggg aaggcccagg ggccaggcaa cccagagggc   480
ccctcttcac tactgccccg gctgctgcca ttactgctcc tgtcaggang ccactcggac   540
aggcggcggc tcttgggtga ggggctacgg ctggcaccac ggcgttcacg gnatgagggc   600
cgtagggcaa gccccaggaa cctgccagtc ccgggctgcg gctgcgtgtc gcttggactt   660
tgccagactg gngctgcngn accttggtgc aaggagctcc agtgtgctgt c            711
```

<210> SEQ ID NO 10
<211> LENGTH: 414
<212> TYPE: DNA
<213> ORGANISM: Homo sapiens
<220> FEATURE:
<221> NAME/KEY: misc_feature
<222> LOCATION: (276)..(276)
<223> OTHER INFORMATION: n=a, c, g or t
<220> FEATURE:
<221> NAME/KEY: misc_feature
<222> LOCATION: (279)..(279)
<223> OTHER INFORMATION: n=a, c, g or t
<220> FEATURE:
<221> NAME/KEY: misc_feature
<222> LOCATION: (352)..(352)
<223> OTHER INFORMATION: n=a, c, g or t
<220> FEATURE:
<221> NAME/KEY: misc_feature
<222> LOCATION: (363)..(363)
<223> OTHER INFORMATION: n=a, c, g or t
<220> FEATURE:
<221> NAME/KEY: misc_feature
<222> LOCATION: (373)..(373)
<223> OTHER INFORMATION: n=a, c, g or t
<220> FEATURE:
<221> NAME/KEY: misc_feature
<222> LOCATION: (389)..(389)
<223> OTHER INFORMATION: n=a, c, g or t
<220> FEATURE:
<221> NAME/KEY: misc_feature
<222> LOCATION: (403)..(403)
<223> OTHER INFORMATION: n=a, c, g or t

<400> SEQUENCE: 10

```
cgacagtgac cagctccatc agctctggga gaaggaccag ctcaacatgg ccaagaacac    60
```

-continued

```
ctggcccatt ctgaagggct ttcaggaggg gcccctcaac ttcgctccca ccttcaagtt      120
tgatgtgggt accaacaaat acgataccag tgccaagaaa cggaagccag cttggacaga      180
ccgtatccta tggaaggtca aggctccagg tgggggtccc agcccctaca ggacggaaga      240
gccaccgact ccaggtgacg cagcacagct taccgnagnc cacatgggaa ttacacagtt      300
caggcgacca aaggcctgt ggctgacccc agtttcctcc ttgcagtttt gnctttcagg       360
ggnacggaca tgncccattg ggttacggnt tggggaggtt cgnccaggtt gcag            414
```

<210> SEQ ID NO 11
<211> LENGTH: 3018
<212> TYPE: DNA
<213> ORGANISM: Homo sapiens

<400> SEQUENCE: 11

```
atggagggcc agagcagcag gggcagcagg aggccaggga cccgggctgg cctgggttcc      60
ctgcccatgc cccagggtgt tgcccaaact ggggcaccct ccaaggtgga ctcaagtttt      120
cagctcccag caaagaagaa cgcagcccta ggaccctcgg aaccaaggtt ggctctggca      180
cctgtagggc cacgggcagc tatgtcagct tcctcggaag gaccgaggct ggctctggca      240
tctccccgac caatcctggc tccactgtgt acccctgaag gcagaaaac agctactgcc       300 caccgcagct ccagcctggc cccaacatct gtgggccagc tggtgatgtc tgcctcagct      360
ggaccaaagc ctcccccagc gaccacaggc tcagttctgg ctccgacgtc cctggggctg      420
gtgatgcctg cctcagcagg gccaagatct cccccagtca ccctgggggcc caatctggcc     480 ccaacctcca gagaccagaa gcaggagcca cctgcctccg tgggacccaa gccaacactg      540
gcagcctctg gcctgagcct ggccctggct tctgaggagc agcccccaga actcccctcc      600 acccctttccc cggtgcccag tccagttctg tctccaactc aggaacaggc cctggctcca      660
gcatccacgg catcaggcgc agcctctgtg gacagacat cagctagaaa gagggatgcc       720
ccagccccta gacctctccc tgcttctgag gggcatctcc agcctccagc tcagacatct      780
ggtcctacag gctcccccacc ctgcatccaa acctccccag accctcggct ctccccctcc      840
ttccgagccc ggcctgaggc cctccacagc agccctgagg atcctgtttt gccacggcca      900
ccccagacct tgcccttgga tgtgggccag ggtccttcag agcctggcac tcactcccct      960
ggacttctgt ccccccacctt ccggcctggg gcccctcag gccagactgt gcccccacct      1020
ctgcccaagc caccccgatc acccagccgt tcccaagcc actccccgaa tcgctctccc       1080
tgtgttcccc cagcccctga catggccctc ccaaggcttg cacacagag tacagggcct       1140 ggcaggtgcc tgagcccaa ccttcaggcc caagaagccc cagccccagt caccaccctcc      1200 tcttctacat ccaccctgtc atcctccccct tggtcagctc agcctacctg gaagagcgac      1260 ccccggcttcc ggatcactgt ggtcacatgg aacgtgggca ctgccatgcc cccagacgat      1320
gtcacatccc tcctccacct gggcggtggt gacgacagcg acggcgcaga catgatcgcc       1380 ataggggttgc aggaagtgaa ctccatgctc aacaagcgac tcaaggacgc cctcttcacg      1440
gaccagtgga gtgagctgtt catggatgcg ctagggccct tcaacttcgt gctggtgagt      1500
tcggtgagga tgcagggtgt catcctgctg ctgttcgcca agtactacca cctgcccttc      1560
ctgcgagacg tgcagaccga ctgcacgcgc actggcctgg gcggctactg gggtaacaag      1620
ggtggcgtga gcgtgcgcct ggcggccttc gggcacatgc tctgcttcct gaactgccac      1680
ttgcctgcgc atatggacaa ggcggagcag cgcaaagaca acttccagac catcctcagc      1740
```

-continued

```
ctccagcagt tccaagggcc gggcgcacag ggcatcctgg atcatgacct cgtgttctgg      1800
ttcggggacc tgaacttccg cattgagagc tatgacctgc actttgtcaa gtttgccatc      1860
gacagtgacc agctccatca gctctgggag aaggaccagc tcaacatggc caagaacacc      1920
tggcccattc tgaagggctt tcaggagggg cccctcaact tcgctcccac cttcaagttt      1980
gatgtgggta ccaacaaata cgataccagt gccaagaaac ggaagccagc ttggacagac      2040
cgtatcctat ggaaggtcaa ggctccaggt gggggtccca gcccctcagg acggaagagc      2100
caccgactcc aggtgacgca gcacagctac cgcagcccac tggaatacac agtcagcgac      2160
cacaagcctg tggctgccca gttcctcctg cagtttgcct tcaggacgac catgccactg      2220
gtgcggctgg aggtggcaga tgagtgggtg cggcccgagc aggcggtggt gaggtaccgc      2280
atggaaacag tgttcgcccg cagctcctgg gactggatcg gcttataccg ggtgggtttc      2340
cgccattgca aggactatgt ggcttatgtc tgggccaaac atgaagatgt ggatgggaat      2400
acctaccagg taacattcag tgaggaatca ctgcccaagg ccatggaga cttcatcctg       2460 ggctactata gtcacaacca cagcatcctc atcggcatca ctgaaccctt ccagatctcg      2520
ctgccttcct cggagttggc cagcagcagc acagacagct caggcaccag ctcagaggga      2580
gaggatgaca gcacactgga gctccttgca cccaagtccc gcagcccag tcctggcaag       2640 tccaagcgac accgcagccg cagcccggga ctggccaggt tccctgggct tgccctacgg      2700
ccctcatccc gtgaacgccg tggtgccagc cgtagcccct caccccagag ccgccgcctg      2760
tcccgagtgg ctcctgacag gagcagtaat ggcagcagcc ggggcagtag tgaagagggg      2820
ccctctgggt tgcctggccc ctgggccttc ccaccagctg tgcctcgaag cctgggcctg      2880
ttgcccgcct tgcgcctaga gactgtagac cctggtggtg gtggctcctg gggacctgat      2940
cgggaggccc tggcgcccaa cagcctgtct cctagtcccc agggccatcg ggggctggag      3000 gaaggggggcc tggggccc                                                   3018
```

<210> SEQ ID NO 12
<211> LENGTH: 1006
<212> TYPE: PRT
<213> ORGANISM: Homo sapiens

<400> SEQUENCE: 12

```
Met Glu Gly Gln Ser Ser Arg Gly Ser Arg Pro Gly Thr Arg Ala
 1               5                  10                  15

Gly Leu Gly Ser Leu Pro Met Pro Gln Gly Val Ala Gln Thr Gly Ala
            20                  25                  30

Pro Ser Lys Val Asp Ser Ser Phe Gln Leu Pro Ala Lys Lys Asn Ala
        35                  40                  45

Ala Leu Gly Pro Ser Glu Pro Arg Leu Ala Leu Ala Pro Val Gly Pro
    50                  55                  60

Arg Ala Ala Met Ser Ala Ser Glu Gly Pro Arg Leu Ala Leu Ala
65                  70                  75                  80

Ser Pro Arg Pro Ile Leu Ala Pro Leu Cys Thr Pro Glu Gly Gln Lys
                85                  90                  95

Thr Ala Thr Ala His Arg Ser Ser Leu Ala Pro Thr Ser Val Gly
            100                 105                 110

Gln Leu Val Met Ser Ala Ser Ala Gly Pro Lys Pro Pro Ala Thr
        115                 120                 125

Thr Gly Ser Val Leu Ala Pro Thr Ser Leu Gly Leu Val Met Pro Ala
    130                 135                 140
```

-continued

```
Ser Ala Gly Pro Arg Ser Pro Pro Val Thr Leu Gly Pro Asn Leu Ala
145                 150                 155                 160

Pro Thr Ser Arg Asp Gln Lys Gln Glu Pro Pro Ala Ser Val Gly Pro
                165                 170                 175

Lys Pro Thr Leu Ala Ala Ser Gly Leu Ser Leu Ala Leu Ala Ser Glu
            180                 185                 190

Glu Gln Pro Pro Glu Leu Pro Ser Thr Pro Ser Pro Val Pro Ser Pro
        195                 200                 205

Val Leu Ser Pro Thr Gln Glu Gln Ala Leu Ala Pro Ala Ser Thr Ala
    210                 215                 220

Ser Gly Ala Ala Ser Val Gly Gln Thr Ser Ala Arg Lys Arg Asp Ala
225                 230                 235                 240

Pro Ala Pro Arg Pro Leu Pro Ala Ser Glu Gly His Leu Gln Pro Pro
                245                 250                 255

Ala Gln Thr Ser Gly Pro Thr Gly Ser Pro Pro Cys Ile Gln Thr Ser
            260                 265                 270

Pro Asp Pro Arg Leu Ser Pro Ser Phe Arg Ala Arg Pro Glu Ala Leu
        275                 280                 285

His Ser Ser Pro Glu Asp Pro Val Leu Pro Arg Pro Pro Gln Thr Leu
    290                 295                 300

Pro Leu Asp Val Gly Gln Gly Pro Ser Glu Pro Gly Thr His Ser Pro
305                 310                 315                 320

Gly Leu Leu Ser Pro Thr Phe Arg Pro Gly Ala Pro Ser Gly Gln Thr
                325                 330                 335

Val Pro Pro Pro Leu Pro Lys Pro Pro Arg Ser Pro Ser Arg Ser Pro
            340                 345                 350

Ser His Ser Pro Asn Arg Ser Pro Cys Val Pro Pro Ala Pro Asp Met
        355                 360                 365

Ala Leu Pro Arg Leu Gly Thr Gln Ser Thr Gly Pro Gly Arg Cys Leu
    370                 375                 380

Ser Pro Asn Leu Gln Ala Gln Glu Ala Pro Ala Pro Val Thr Thr Ser
385                 390                 395                 400

Ser Ser Thr Ser Thr Leu Ser Ser Ser Pro Trp Ser Ala Gln Pro Thr
                405                 410                 415

Trp Lys Ser Asp Pro Gly Phe Arg Ile Thr Val Val Thr Trp Asn Val
            420                 425                 430

Gly Thr Ala Met Pro Pro Asp Asp Val Thr Ser Leu Leu His Leu Gly
        435                 440                 445

Gly Gly Asp Asp Ser Asp Gly Ala Asp Met Ile Ala Ile Gly Leu Gln
    450                 455                 460

Glu Val Asn Ser Met Leu Asn Lys Arg Leu Lys Asp Ala Leu Phe Thr
465                 470                 475                 480

Asp Gln Trp Ser Glu Leu Phe Met Asp Ala Leu Gly Pro Phe Asn Phe
                485                 490                 495

Val Leu Val Ser Ser Val Arg Met Gln Gly Val Ile Leu Leu Leu Phe
            500                 505                 510

Ala Lys Tyr Tyr His Leu Pro Phe Leu Arg Asp Val Gln Thr Asp Cys
        515                 520                 525

Thr Arg Thr Gly Leu Gly Gly Tyr Trp Gly Asn Lys Gly Gly Val Ser
    530                 535                 540

Val Arg Leu Ala Ala Phe Gly His Met Leu Cys Phe Leu Asn Cys His
545                 550                 555                 560

Leu Pro Ala His Met Asp Lys Ala Glu Gln Arg Lys Asp Asn Phe Gln
```

```
                          565                 570                 575
Thr Ile Leu Ser Leu Gln Gln Phe Gln Gly Pro Gly Ala Gln Gly Ile
                580                 585                 590

Leu Asp His Asp Leu Val Phe Trp Phe Gly Asp Leu Asn Phe Arg Ile
            595                 600                 605

Glu Ser Tyr Asp Leu His Phe Val Lys Phe Ala Ile Asp Ser Asp Gln
        610                 615                 620

Leu His Gln Leu Trp Glu Lys Asp Gln Leu Asn Met Ala Lys Asn Thr
625                 630                 635                 640

Trp Pro Ile Leu Lys Gly Phe Gln Glu Gly Pro Leu Asn Phe Ala Pro
                645                 650                 655

Thr Phe Lys Phe Asp Val Gly Thr Asn Lys Tyr Asp Thr Ser Ala Lys
            660                 665                 670

Lys Arg Lys Pro Ala Trp Thr Asp Arg Ile Leu Trp Lys Val Lys Ala
        675                 680                 685

Pro Gly Gly Gly Pro Ser Pro Ser Gly Arg Lys Ser His Arg Leu Gln
    690                 695                 700

Val Thr Gln His Ser Tyr Arg Ser His Met Glu Tyr Thr Val Ser Asp
705                 710                 715                 720

His Lys Pro Val Ala Ala Gln Phe Leu Leu Gln Phe Ala Phe Arg Asp
                725                 730                 735

Asp Met Pro Leu Val Arg Leu Glu Val Ala Asp Glu Trp Val Arg Pro
            740                 745                 750

Glu Gln Ala Val Val Arg Tyr Arg Met Glu Thr Val Phe Ala Arg Ser
        755                 760                 765

Ser Trp Asp Trp Ile Gly Leu Tyr Arg Val Gly Phe Arg His Cys Lys
    770                 775                 780

Asp Tyr Val Ala Tyr Val Trp Ala Lys His Glu Asp Val Asp Gly Asn
785                 790                 795                 800

Thr Tyr Gln Val Thr Phe Ser Glu Glu Ser Leu Pro Lys Gly His Gly
                805                 810                 815

Asp Phe Ile Leu Gly Tyr Tyr Ser His Asn His Ser Ile Leu Ile Gly
            820                 825                 830

Ile Thr Glu Pro Phe Gln Ile Ser Leu Pro Ser Ser Glu Leu Ala Ser
        835                 840                 845

Ser Ser Thr Asp Ser Ser Gly Thr Ser Ser Glu Gly Glu Asp Asp Ser
    850                 855                 860

Thr Leu Glu Leu Leu Ala Pro Lys Ser Arg Ser Pro Ser Pro Gly Lys
865                 870                 875                 880

Ser Lys Arg His Arg Ser Arg Ser Pro Gly Leu Ala Arg Phe Pro Gly
                885                 890                 895

Leu Ala Leu Arg Pro Ser Ser Arg Glu Arg Arg Gly Ala Ser Arg Ser
            900                 905                 910

Pro Ser Pro Gln Ser Arg Arg Leu Ser Arg Val Ala Pro Asp Arg Ser
        915                 920                 925

Ser Asn Gly Ser Ser Arg Gly Ser Ser Glu Glu Gly Pro Ser Gly Leu
    930                 935                 940

Pro Gly Pro Trp Ala Phe Pro Ala Val Pro Arg Ser Leu Gly Leu
945                 950                 955                 960

Leu Pro Ala Leu Arg Leu Glu Thr Val Asp Pro Gly Gly Gly Ser
                965                 970                 975

Trp Gly Pro Asp Arg Glu Ala Leu Ala Pro Asn Ser Leu Ser Pro Ser
            980                 985                 990
```

```
Pro Gln Gly His Arg Gly Leu Glu   Glu Gly Gly Leu Gly  Pro
        995              1000                1005
```